United States Patent [19]

Daynes et al.

[11] Patent Number: 5,824,313
[45] Date of Patent: Oct. 20, 1998

[54] VACCINE COMPOSITIONS AND METHOD FOR INDUCTION OF MUCOSAL IMMUNE RESPONSE VIA SYSTEMIC VACCINATION

[75] Inventors: Raymond A. Daynes, Park City; Barbara A. Araneo, Salt Lake City, both of Utah

[73] Assignee: University of Utah Research Foundation, Salt Lake City, Utah

[21] Appl. No.: 480,567

[22] Filed: Jun. 7, 1995

Related U.S. Application Data

[63] Continuation-in-part of Ser. No. 123,844, Sep. 9, 1993, Pat. No. 5,518,725, which is a continuation-in-part of Ser. No. 13,972, Feb. 4, 1993, abandoned, and Ser. No. 779,499, Oct. 18, 1991, abandoned, which is a continuation-in-part of Ser. No. 412,270, Sep. 25, 1989, Pat. No. 5,540,919.

[51] Int. Cl.$^6$ ........................ A61K 39/00; A61K 39/145; A61K 39/155; A61K 39/07
[52] U.S. Cl. .................................... 424/184.1; 424/209.1; 424/211.1; 424/212.1; 424/245.1; 514/167
[58] Field of Search ............................. 424/212.1, 209.1, 424/211.1, 184.1, 245.1; 514/167

[56] References Cited

U.S. PATENT DOCUMENTS

| | | |
|---|---|---|
| 4,698,221 | 10/1987 | Straub . |
| 5,077,284 | 12/1991 | Loria et al. . |
| 5,098,899 | 3/1992 | Gilbert et al. . |
| 5,206,008 | 4/1993 | Loria . |
| 5,407,684 | 4/1995 | Loria et al. . |
| 5,518,725 | 5/1996 | Daynes et al. ........................ 424/212.1 |

FOREIGN PATENT DOCUMENTS

| | | |
|---|---|---|
| 2 204 237 | 11/1988 | United Kingdom . |
| WO 91/04030 | 4/1991 | WIPO . |

OTHER PUBLICATIONS

Abe, J. et al. (1989). "A Synthetic Analogue of Vitamin $D_3$, 22–Oxa–1α25–Dihydroxyvitamin $D_3$, is a Potent Modulator of In vivo Immunoregulating Activity Without Inducing Hypercalcemia in Mice," *Endocrinol.* 124:2645–2647.
Abraham, E. et al. (1992). "Intranasal Immunization with Liposomes Containing IL–2 Enhances Bacterial Polysaccharide Antigen–Specific Pulmonary Secretory Antibody Response," *J. Immunol.* 149:3719–3726.
Araneo, B.A. et al. (1991). "Dihydrotestosterone Exerts a Depressive Influence on the Production of Interleukin–4 (IL–4), IL–5, and γ–Interferon, But Not IL–2 by Activated Murine T Cells," *Blood* 78:688–699.
Araneo, B. A. et al. (1993). "Administration of Dehydroepiandrosterone to Burned Mice Preserves Normal Immunologic Competence," *Arch. Surg.* 128:318–325.
Araneo, B.A. et al. (1993). "Reversal of the Immunosenescent Phenotype by Dehydroepiandrosterone: Hormone Treatment Provides an Adjuvant Effect on the Immunization of Aged Mice with Recombinant Hepatitis B Surface Antigen," *J. Infect. Dis.* 167:830–840.

AyanlarBatuman, O. et al. (1991). "Regulation of Transforming Growth Factor–β1 Gene Expression by Glucocorticoids in Normal Human T Lymphocytes," *J. Clin. Invest.* 88:1574–1580.
Bhalla, A.K. (1989). "Hormones and the Immune Response," *Am. of Rheumatic Dis.* 48:1–6.
Bienenstock, J. et al. (1983). "Regulation of Lymphoblast Traffic and Localization in Mucosal Tissues, with Emphasis on IgA," *Federation Proceedings* 42:3213–3217.
Bikle, D.D. (1992). "Clinical counterpoint: Vitamin D: New Actions, New Analogs, New Therapeutic Potential," *Endocrine Reviews* 13:765–784.
Binderup, L. et al. (1992). "Commentary: Immunological Properties of Vitamin D Analogues and Metabolites," *Biochem. Pharmacol.* 43:1885–1892.
Casson, P.R. et al. (1993). "Oral Dehydroepiandrosterone in Physiologic Doses Modulates Immune Function in Postmenopausal Women,"0 *Am. J. Obstet. Gynecol.* 169:1536–1539.
Coffman, R.L. (1989). "T–Helper Heterogeneity and Immune Response Patterns," *Hosp. Practice* (Aug. 15, 1989):101–133.
Coffman, R.L. et al. (1989). "Transforming Growth Factor β Specifically Enhances IgA Production by Lipopolysaccharide–Stimulated Murine B Lymphocytes," *J. Exp. Med.* 170:1039–1044.

(List continued on next page.)

*Primary Examiner*—James C. Housel
*Assistant Examiner*—Rodney P. Swartz
*Attorney, Agent, or Firm*—Venable, Baetjer, Howard & Civiletti, LLP

[57] ABSTRACT

The invention relates to a vaccine which comprises an antigen and a lymphoid organ modifying agent. Suitable lymphoid organ modifying agents include, but are not limited to, 1,25-dihydroxy Vitamin $D_3$, biologically active Vitamin $D_3$ derivatives which are capable of activating the intracellular Vitamin $D_3$ receptor, all trans-retinoic acid, retinoic acid derivatives, retinol, retinol derivatives and glucocorticoid. The vaccine composition may further comprise an immune response augmenting agent. The immune response augmenting agent enhances T cell lymphokine production. Suitable immune response augmenting agents include, but are not limited to, dehydroepiandrosterone (DHEA), DHEA congeners and DHEA-derivatives. The invention also relates to a method for inducing an antigen-specific mucosal immune response in a subject vertebrate animal which comprises administering a vaccine which comprises an antigen and a lymphoid organ modifying agent to a site which drains into a peripheral lymph compartment. Alternatively, the method comprises separately administering the lymphoid organ modifying agent and a vaccine containing an antigen to the same site. The method may further comprise additionally administering an immune response augmenting agent which enhances T cell lymphokine production. The immune response augmenting agent may be administered sequentially or contemporaneously with the lymphoid organ modifying agent.

61 Claims, 24 Drawing Sheets

OTHER PUBLICATIONS

Dawson, M.I. et al. (1981). "Aromatic Retinoic Acid Analogues. Synthesis and Pharmacological Activity," *J. Med. Chem.* 24:583–592.

Dawson, M.I. et al. (1981). "Retinoci Acid Analogues with Ring Modifications. Synthesis and Pharmacological Activity," *J. Med. Chem.* 24:1214–1223.

Daynes, R.A. et al. (1989). "Contrasting Effects of Glucocorticoids on the Capacity of T. Cells to Produce the Growth Factors Interleukin 2 and Interleukin 4," *Eur. J. Immunol.* 19:2319–2325.

Daynes, R.A. et al. (1990). "Regulation of Murine Lymphokine Production In Vivo: II. Dehydroepiandrosterone is a Natural Enhancer of Interleukin 2 Synthesis by Helper T Cells," *Eur. J. Immunol.* 20:793–802.

Daynes, R.A. et al. (1990). "Regulation of Murine Lymphokine Production In Vivo: III. The Lymphoid Tissue Microenvironment Exerts Regulatory Influences Over T Helper Cell Function," *J. Exp. Med.* 171:979–996.

Daynes, R.A. et al. (1991). "Locally active steroid hormones may facilitate compartmentalization of immunity by regulating the types of lymphokines produce by helper T cells," *Research in Immunology* 142:40–45.

Daynes, R.A. and Araneo, B.A. (1992). "Prevention and Reversal of some Age–Associated Changes in Immunologic Responses by Supplemental Dehydroepiandrosterone Sulphate Therapy," *Aging: Immunology and Infectious Disease* 3:135–154.

Daynes, R.A. et al. (1992). "Natural Regulators of T–Cell Lymphokine Production In Vivo," *J. Immunother.* 12:174–179.

Defrance, T. et al. (1992). "Interleukin 10 and Transforming Growth Factor β Co–Operate to Induce Anti–CD40–Activated naive Human B Cells to Secrete Immunoglobulin A," *J. Exp. Med.* 175:671–682.

Dinarello, C.A. et al. (1987). "Current Concepts: Lymphokines," *New Eng. J. Med.* 317:940–945.

Ernst, P.B. et al. (1987). "Immunithy in Mucosal Tissues," in *Basic & Clinical Immunology,* Sixth Ed. (eds. Stites, D.P. et al.), (Appleton & Lange, Norwalk, CT), pp. 159–166.

Finkelman, F.D. et al. (1990). "Lymphokine Control of In Vivo Immunoglobulin Isotype Selection," *Ann. Rev. Immunol.* 8:303–333.

Finkelman, R.D. et al. (1991). "Vitamin D deficiency causes a selective reduction in deposition of transforming growth factor β in rat bone: Possible mechanism for impaired osteoinduction," *Proc. Natl. Acad. Sci. USA* 88:3657–3660.

Garg, M. et al. (1993). "Reversal of Age–Associated Decline in Immune Response to Pnu–Immune Vaccine by Supplementation with the Steroid Hormone Dehydroepiandrosterone," *Infect. Immun.* 61:2238–2241.

Glick, A.B. et al. (1989). "Retinoic acid induces transforming growth factr–β2 in cultural keratinocytes and mouse epidermis," *Cell Regulation* 1:87–97.

Granner, D.K. (1988). "Hormones of the Adrenal Cortex," *Harper's Biochemistry,* pp. 511–523.

Hahn–Zoric, M. et al. (1989). "The Influence on the Secretory IgA Antibody Levels in Lactating Women of Oal Typhoid and Parenteral Cholera Vaccines Given Alone or in Combination," *Scand. J. Infect. Dis.* 21:421–426.

Hewison, M. (1992). "Vitamin D and the Immune System," *J. Endocrinol.* 132:173–175.

Holmgren, J. (1991). "Mucosal immunity and vaccination," *FEMS Microbiology Immunology* 89:1–10.

Kawanishi, H. et al. (1983). "Mechanisms Regulating IgA Class–Specific Immunoglobulin Production in Murine Gut–Associated Lymphoid Tissues," *J. Exp. Med.* 157:433–450.

Kiyono, H. et al. (1984). "Isotype Specificity of Helper T Cell Clones," *J. Exp. Med.* 159:798–811.

Komori, T. et al. (1985). "The Effect of 1α–Hydroxyvitamin $D_3$ on Primary Antibody Formation in Mice," *Immunopharmacol.* 9:141–146.

Lebman, D.A. et al. (1990). "Molecular Characterization of Germ–Line Immunoglobulin A Transcripts Produced During Transforming Growth Factor Type β–Induced Isotype Switching," *Proc. Natl. Acad. Sci. USA* 87:3962–3966.

Lebman, D.A. et al. (1990). "Mechanism for Transforming Growth Factor β and IL–2 Enhancement of IgA Expression in Lipopolysaccharide–Stimulated B Cell Cultures," *J. Immunology* 144:952–959.

Lemire, J.M. (1992). "Immunomodulatory Role of 1,25–Dihydroxyvitamin $D_3$," *J. Cell. Biochem.* 49:26–31.

Liew, F.Y. et al. (1984). "Cross–protection in mice infected with influenza A virus by the respiratory route is correlated with local IgA antibody rather than serum antibody or cytotoxic T cell reactivity," *Eur. J. Immunol.* 14:350–356.

Loria, R.M. and Padgett, D.A. (1992). "Mobilization of Cutaneous Immunity for Systemic Protection Against Infections," *Ann. N.Y. Acad. Sci.* 650:363–366.

Mbawuike, I.N. et al. (1990). "Enhancement of the Protective Efficacy of Inactivated Influenza A Virus Vaccine in Aged Mice by IL–2 Liposomes," *Vaccine* 8:347–352.

McBride, B.W. et al. (1988). "Mucosal antibody response to vaginal infection with herpes simplex virus in pre–vaccinated guinea–pigs," *Vaccine* 6:414–418.

Meikle, A.W. et al. (1991). "Adrenal Androgen Secretion and Biologic Effects," *Endocrin. Metab. Clin. N. Am.* 20:381–400.

Mestecky, J. (1987). "The Common Mucosal System and Current Strategies for Induction of Immune Responses in External Secretions," *J. Clin. Immunol.* 7:265–276.

Müller, K. et al. (1992). "Inhibition of Human T Lymphocyte Proliferation and Cytokine Production by 1,25–dihydroxyvitamin D3, Differential Effects on CD45RA+ and CD45RO+ Cells," *Autoimmunity* 14:37–43.

Murray, R.K. et al. (eds.) (1988). *Harper's Biochemistry* (21st Edition), pp. 507–508 (Appleton & Lange, Norwalk, CT).

Nossal, G.J.V. (1987). "Current Concepts: Immunology: The Basic Components of the Immune System," *New Eng. J. Med.* 316:1320–1325.

Nunberg, J.H. et al. (1989). "Interleukin 2 Acts as an Adjuvant to Increase the Potency of Inactivated Rabies Virus Vaccine," *Proc. Natl. Acad. Sci. USA* 86:4240–4243.

Petkovich, P.M. et al. (1987). "1,25–Dihydroxyvitamin D3 Increases Epidermal Growth Factor Receptors and Transforming Growth Factor β–Like Activity in a Bone–Derived Cell Line," *J. Biol. Chem.* 262:13424–13428.

Pfeilschifter, J. et al. (1987). "Modulation of Type β Transforming Growth Factor Activity in Bone Cultures by Osteotropic Hormones," *Proc. Natl. Acad. Sci. USA* 84:2024–2048.

Quiding, M. et al. (1991). "Intestinal Immune Responses in Humans," *J. Clin. Invest.* 88:143–148.

Rasmussen, K.R. et al. (1992). "Dehydroepiandrosterone–Induced Reduction of Cryptosporidium Parvum Infections in Aged Syrian Golden Hamsters," *J. Parasitol.* 78:554–557.

Rigby, W.F.C. (1988). "The Immunobiology of Vitamin D," *Immunol. Today* 9:54–57.

Risdon, G. et al. (1990). "Mechanisms of Chemoprevention by Dietary Dehydroisoandrosterone: Inhibition of Lymphopoiesis," *Am. J. Pathol.* 136:759–769.

Roberts, A.B. et al. (1992). "Mechanistic Interrelationships Between Two Superfamilies: The Steroid/Retinoid Receptors and Transforming Growth Factor–β," *Cancer Surveys* 14:205–220.

Roitt, I.M. (1988). *Essential Immunology*, Blackwell Scientific Publications, p. 172.

Shull, M.M. et al. (1992). "Targeted Disruption of the Mouse Transforming Growth Factor–β–1 Gene Results in Multifocal Inflammatory Disease," *Nature* 359:693–699.

Suzuki, T. et al. (1991). "Dehydroepiandrosterone Enhances IL2 Production and Cytotoxic Effector Function of Human T Cells," *Clin. Immunol. Immunopathol.* 61:202–211.

Tabata, T. et al. (1986). "The Effect of 1α–Hydroxyvitamin $D_3$ on Cell–Mediated Immunity in Hemodialyzed Patients," *J. Clin. Endocrin. Metab.* 63:1218–1221.

van den Wall Bake, A.W.L. et al. (1992). "Transforming Growth Factor–β Inhibits the Production of IgG, IgM, and IgA in Human Lymphocyte Cultures," *Cellular Immunology* 144:417–428.

van Vlasselaer, P. et al. (1992). "Transforming Growth Factor–β Directs IgA Switching in Human B Cells," *J. Immunol.* 148:2062–2067.

Weinberg, A. et al. (1988). "Recombinant Interleukin 2 as an Adjuvant for Vaccine–Induced Protection," *J. Immunol.* 140:294–299.

Weindruch, R. et al. (1984). "Food Intake Reduction and Immunologic Alterations in Mice Fed Dehydroepiandrosterone," *Exp. Gerontol.* 19:297–304.

Weksler, M.E. (1993). "Immune senescence and adrenal steroids: immune dysregulation and the action of dehydroepiandrosterone (DHEA) in old animals," *Eur. J. Clin. Pharmacol.* 45[*Suppl. 1*]:S21–S23.

Wiedmeier, S.E. et al. (1991). "Thymic Modulation of IL–2 and IL–4 Synthesis by Peripheral T Cells," *Cell. Immunol.* 135:501–518.

Windholz, M. et al. (eds.) (1976). *The Merck Index*, pp. 1289–1291 (Merck & Co., Inc., Rahway, N.J.).

Wu, C.Y. et al. (1991). "Glucocorticoids Suppress the Production of Interleukin 4 by Human Lymphocytes," *Eur. J. Immunol.* 21:2645–2647.

Minghett, et al., "1,25$(OH)_2$–Vitamin $D_3$ Receptors: Gene Regulation and Genetic Circuitry" FASEB J. 2:3043–3053, 1988.

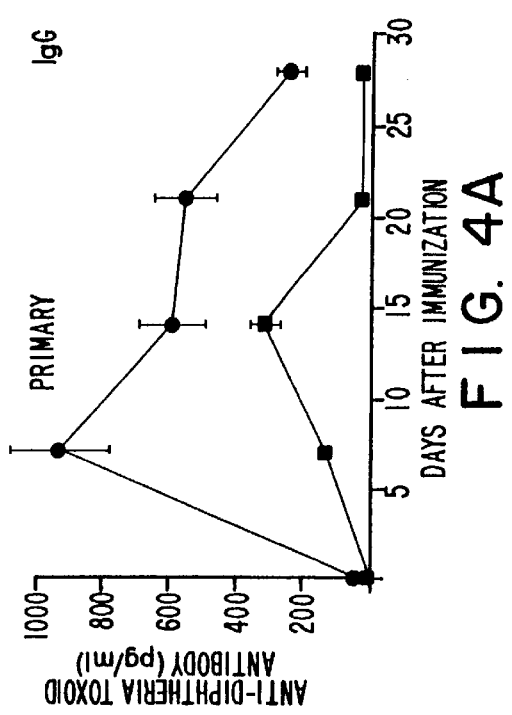
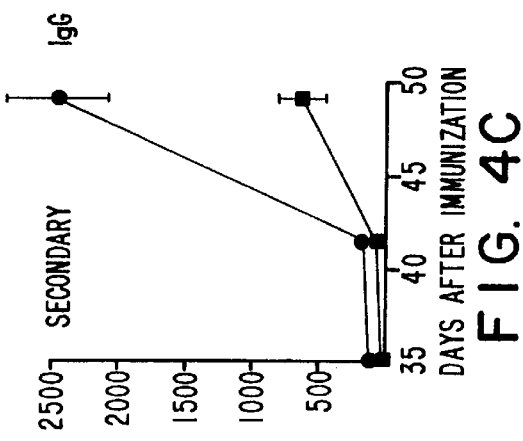
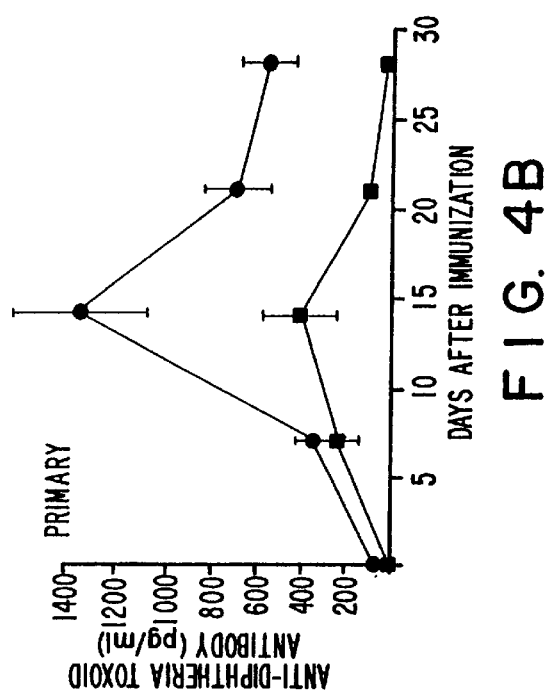
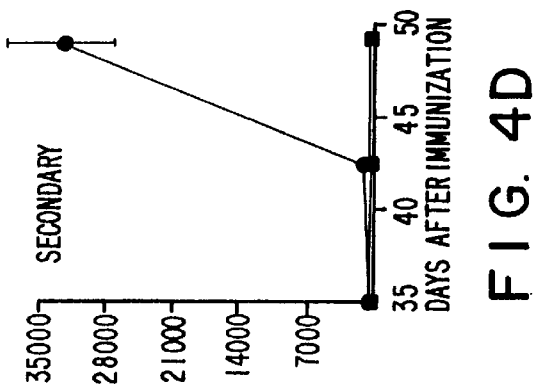

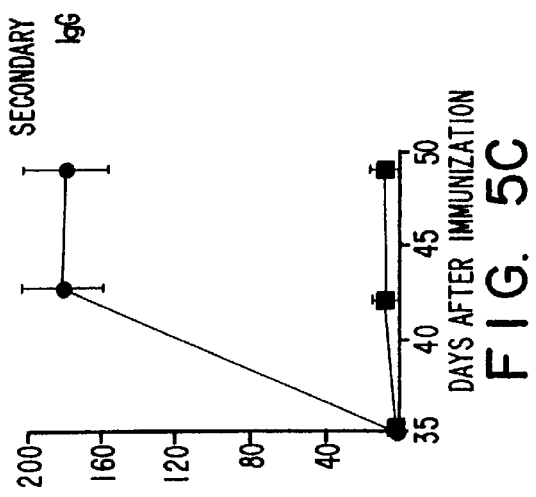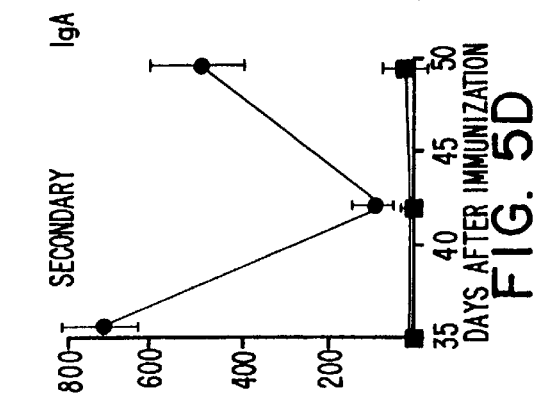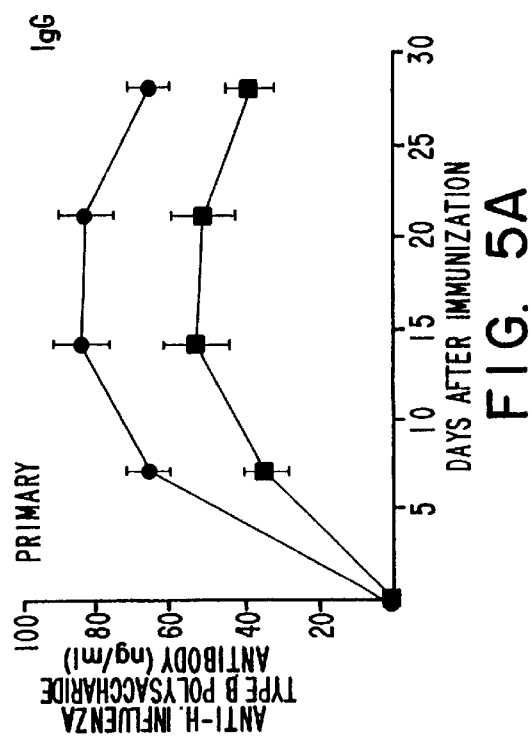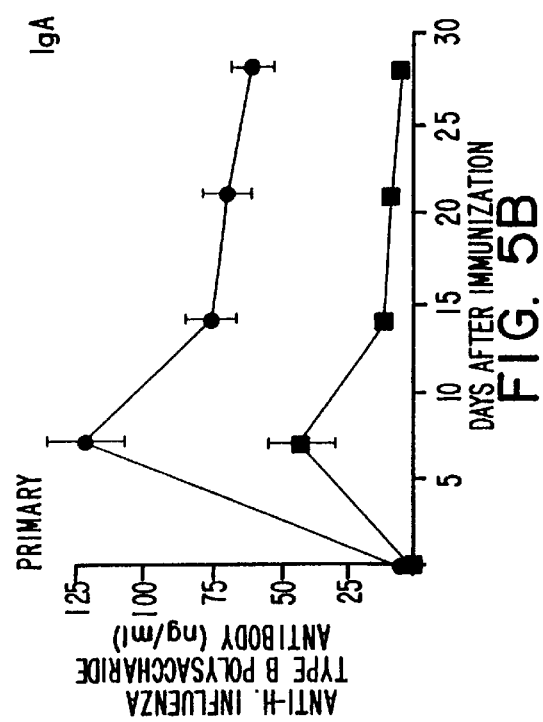

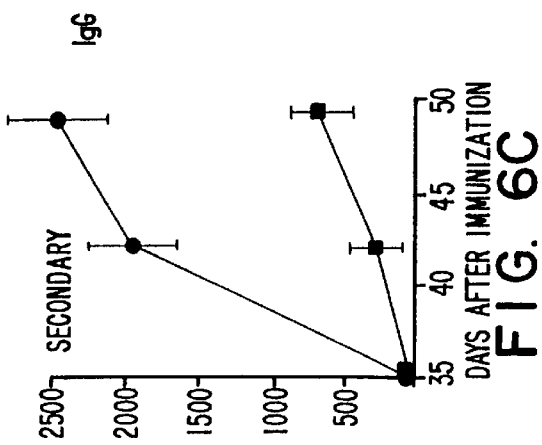
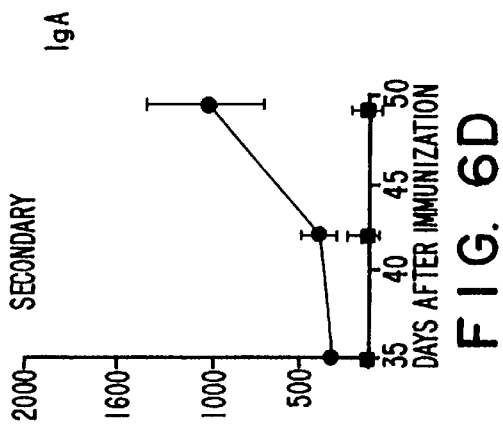
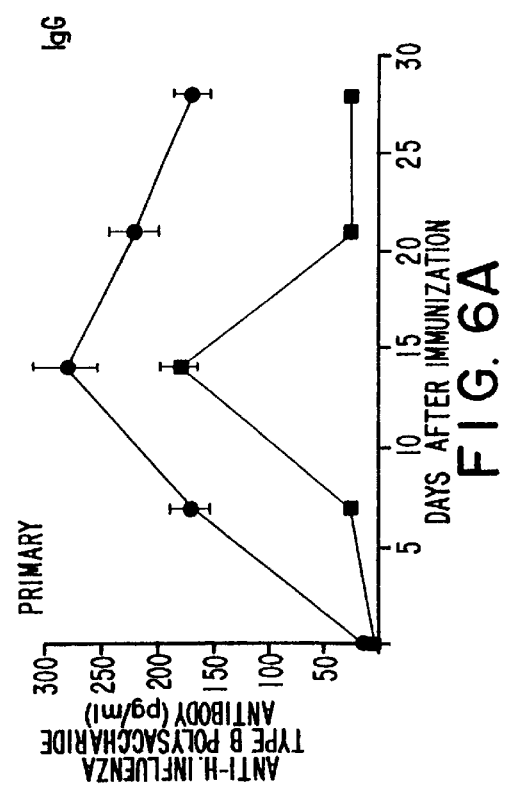
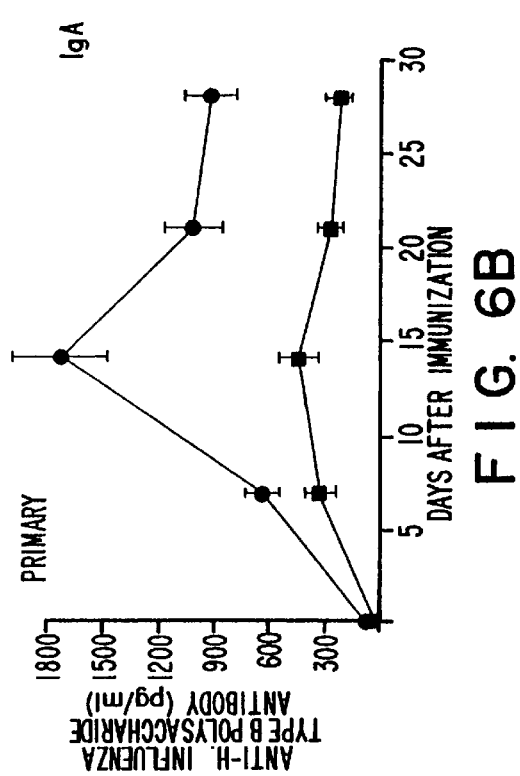

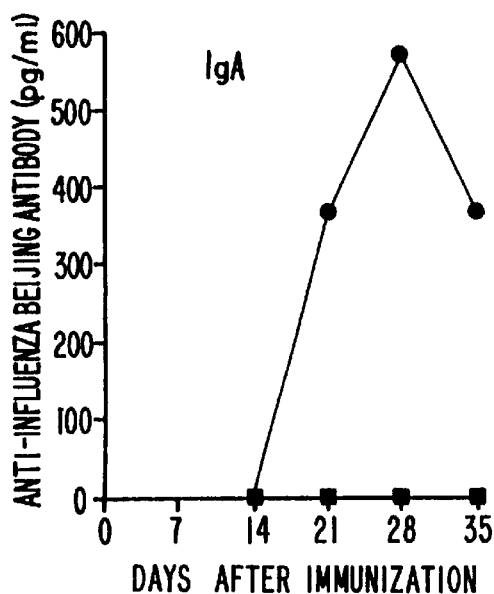
F I G. 11A
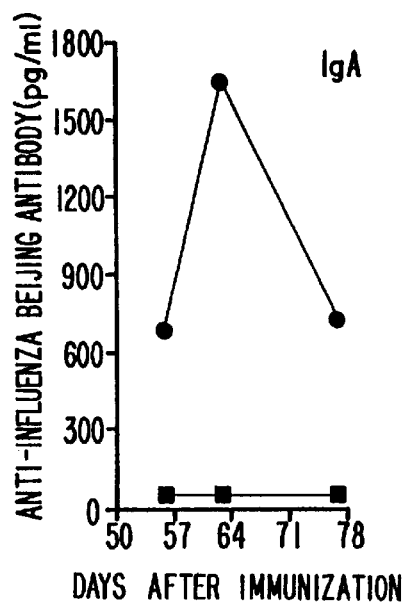
F I G. 11B
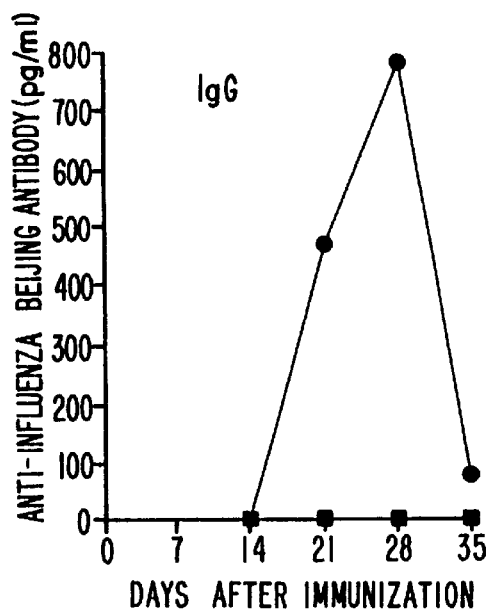
F I G. 11C
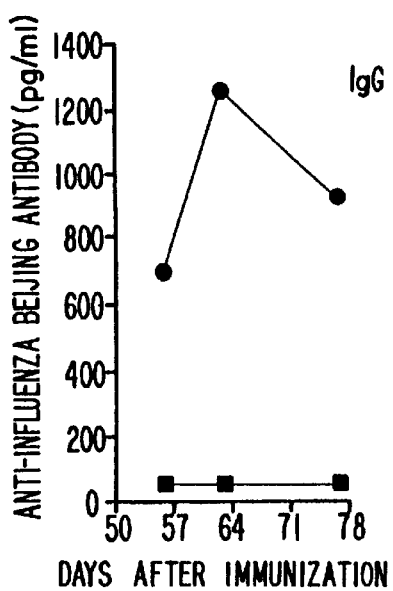
F I G. 11D

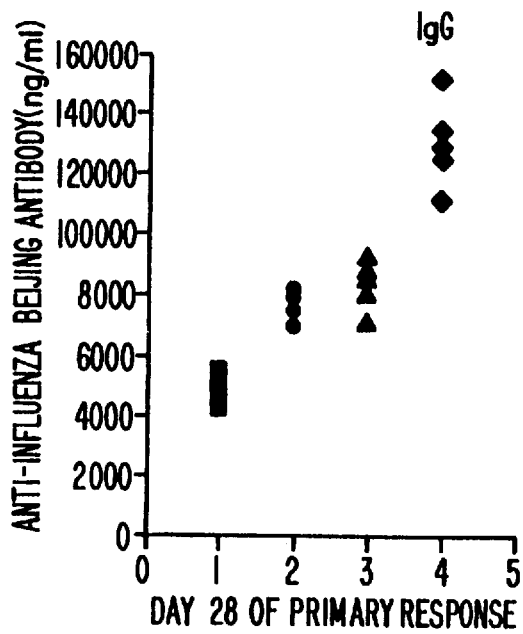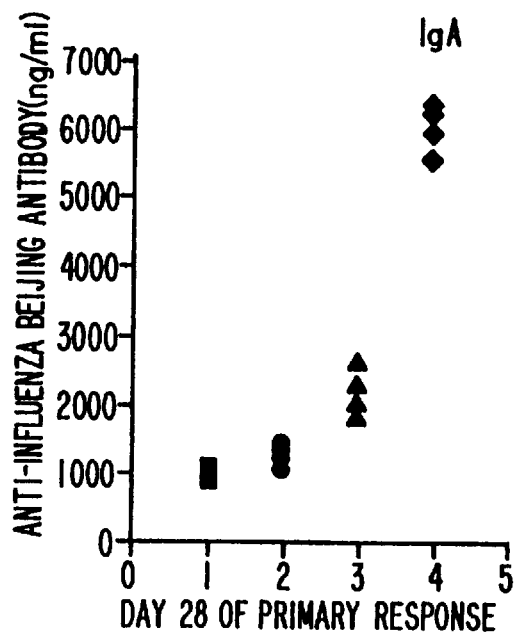
FIG. 13A
FIG. 13B
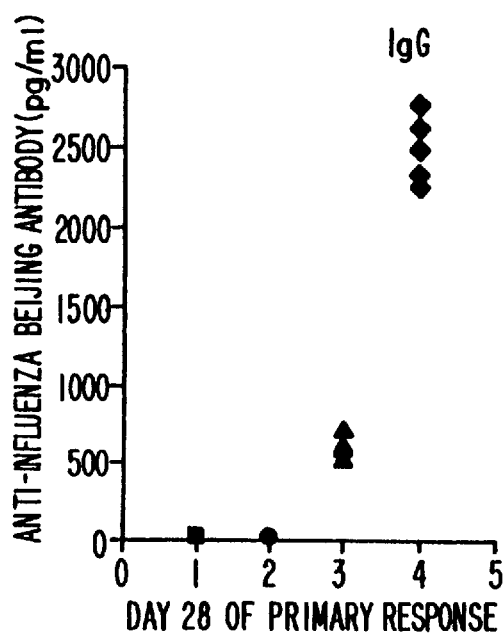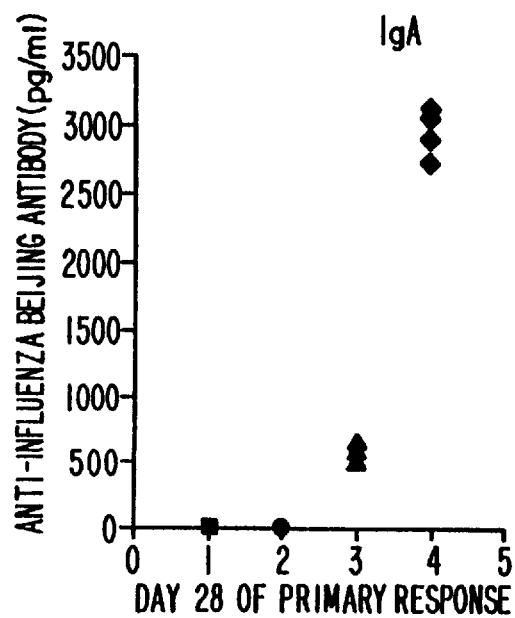
FIG. 13C
FIG. 13D 1 ug 'F' PROTEIN +
0.1 ug D3

LOG 2 RSV NASAL WASH NEUTRALIZATION TITERS 1 ug 'F' PROTEIN    NONIMMUNE CONTROL

POST-CHALLENGE (DAY +3)
2 x 10⁵ PFU RSV A2 STRAIN

FIG. 21

VACCINE COMPOSITIONS AND METHOD FOR INDUCTION OF MUCOSAL IMMUNE RESPONSE VIA SYSTEMIC VACCINATION

CROSS-REFERENCE TO RELATED APPLICATIONS

This Application is a continuation-in-part of U.S. application Ser. No. 08/123,844, filed Sep. 9, 1993, now U.S. Pat. No. 5,518,725, which in turn is a continuation-in-part of U.S. application Ser. No. 08/013,972, filed Feb. 4, 1993, now abandoned, and of U.S. application Ser. No. 07/779,499, filed Oct. 18, 1991, now abandoned. Ser. No. 07/779,499 is a continuation-in-part of U.S. application Ser. No. 07/412,270, filed Sep. 25, 1989 now U.S. Pat. No. 5,540,919. The specification of each of these applications is incorporated by reference herein in its entirety.

TECHNICAL FIELD

The invention relates to vaccine compositions and methods of vaccination which provide for the induction of mucosal immune responses.

BACKGROUND OF THE INVENTION

The publications and other materials used herein to illuminate the background of the invention, or provide additional details respecting its practice, are incorporated by reference.

The Mucosal Immune Response

The vast majority of agents of infection in vertebrates enter the host across a mucosal surface, including generally the mucosa of the alimentary canal (including oral mucosa), the respiratory tract (including olfactory and conjunctival mucosa), the mammary glands, and the genitourinary tract. The common mucosal immune system, by way of the secretory immunoglobulin response, provides a first line of resistance to infection across mucosal surfaces in vertebrates (J. Mestecky (1987). *J Clin. Immunol.* 7:265–75).

The secretory immune response entails, among other events, clonal proliferation of antigen-specific B cells and progressive isotype switching by the B cell progeny to all subclasses of IgG- and IgA-secreting cells. Antigens such as microorganisms, proteins, polysaccharides, etc., that are encountered at a mucosal site can elicit local production of antibodies into the secretions that bathe the mucosal surface at the site, as well as other mucosal sites.

It is well established that in many species, including humans, the daily combined production of secretory and circulating IgA exceeds that of other immunoglobulin isotypes. Secretory IgA as well as IgM and all subclasses of IgG have been found in virtually all external secretions, including tears, saliva, colostrum and milk, and in the mucous secretions of the respiratory, intestinal and genitourinary tracts. In most species, the systemic and secretory production of immunoglobulins maintain a considerable degree of independence. For example, in humans, the majority of serum IgA is produced in the bone marrow, and is not found in secretions. The vast majority of secretory IgA is produced by plasma cells distributed in the lamina propria of the common mucosal epithelia of the body. Furthermore, locally produced secretory IgA does not contribute significantly to the circulating pool of IgA. The IgA of secreted body fluids is known to be assembled within IgA-producing cells in a polymeric form before selective transport to external surfaces. The IgA present in plasma and in cerebrospinal fluid is predominantly monomeric in structure (i.e., approximately 7–8S), while the majority of the secreted forms of IgA are dimeric.

The protective role of secretory IgA has been well demonstrated in both clinical and experimental systems. As a potent mechanism for the prevention of infectious diseases and for the inhibition of allergic reactions at mucosal surfaces, secreted IgA neutralizes biologically active antigens, prevents uptake of antigens from the intestinal tract, inhibits adherence of bacteria to epithelial surfaces and enhances the antibacterial effects of the innate defense system (see J. Mestecky (1987), supra). Numerous studies have determined that the mucosa are endowed with a specialized lymphoid tissue which induces and regulates the immune response of external secretions. The gut-associated lymphoreticular tissue ("GALT") includes both the Peyer's Patches, which are distinct lymphoid nodules along the small intestines, and the solitary lymphoid nodules. Lymphoid nodules bear a characteristic histologic organization with an epithelium comprised of cuboidal epithelial cells and microfold cells ("M cells"). M cells possess numerous cytoplasmic vesicles and cytoplasmic extensions which surround the lymphoreticular cells in the underlying region, called the dome. It is thought that M cells serve as an antigen-sampling mechanism for the uptake of lumenal antigens and their intact transport across the epithelium. The dome area is rich in MHC class II$^+$ cells (macrophages, dendritic cells and B cells), which should create a superb environment for the important function of antigen presentation. The dome also contains many T cells, the function of which is not well-defined. Underneath the dome are situated two follicle areas which represent B cell zones enriched in B cells that can become committed to IgA production. However, unlike germinal centers in other secondary lymphoid tissue, B cell development and differentiation into plasma cells rarely occur in this tissue.

Once antigen penetrates the mucosal epithelial cells, antigen-presenting cell-dependent activation of paracortical T cells and germinal center B cells within the Peyer's Patches is observed. However, the inductive stimuli required for differentiation of IgA-committed B cells is deferred until B cells have migrated through efferent lymphatics into the mesenteric lymph nodes after departure from the Peyer's Patches. Ultimately, IgA-committed, antigen-sensitized B cells enter the circulation through the lymph to populate various exocrine glands and mucosal epithelia throughout the body. Under local influences which include information provided by helper T cells, by the antigen and other biochemical mediators, terminal differentiation into IgA-secreting plasma cells occurs.

The microenvironment of the Peyer's Patch, which favors development of IgA-committed B cells, has been a focal point of research on the mucosal immune system (J. Bienenstock et al. (1983). *Fed. Proc.* 42:3215–17; J. Mestecky (1987), supra). The process of isotype-switching which commits Peyer's Patch B cells to IgA production is known to be under the regulation of T cells and specialized T cell effector function (J. Bienenstock et al. (1983), supra). A natural distribution in the pattern of cytokines made by T cells in distinct lymphoid compartments is emerging from recent work (R. Daynes et al. (1990). *J Exp. Med.* 171:979–96; B. Araneo et al. (1993). *J. Inf. Diseases* 167:830–840). T cells residing in lymphoid tissue that receives drainage from the skin (that is, from peripheral lymph nodes) produce high levels of IL-2 and IFN-γ when activated. T cells isolated from lymphoid tissue, including Peyer's Patch, that receive their primary drainage from mucosal surfaces (mucosal lymph nodes) produce a pattern of cytokines enriched in IL-4 and IL-5, but low in IL-2 and IFN-γ, following activation. The ability of cytokines to direct immunoglobulin class switching by activated B cells is a well-studied and well-accepted phenomenon. See, e.g., Finkelman et al. (1990). *Ann. Rev. Immunol.* 8:303–34. In several cases, the molecular mechanism regulating immunoglobulin class-switching has been defined (Finkelman et al. (1990), supra). Investigations by Kiyono et al. ((1984). *J Exp. Med.* 159:798–811) and H. Kawanishi et al. ((1983). *J Exp. Med.* 157:433–50) indicate that Peyer's Patch T cells cause switching of IgM-bearing B cells to IgA-bearing B cells. These "switch" T cells do not facilitate class-switching of IgG-bearing B cells to IgA-bearing. Importantly, antigen-specific Peyer's Patch-derived T cell clones are able to mediate maturation and differentiation of IgA-bearing B cells into IgA-secreting cells. Kiyono et al., supra, concluded that growth and differentiation factors made by antigen-specific Peyer's Patch T cells is responsible for the selective enhancement of IgA at gut mucosal surfaces.

As a consequence of the major emphasis on the specialized function and lymphokine-producing potential of Peyer's Patch T cells in the initiation of the mucosal immune process, research in this important field has centered on the delivery of antigen across mucosal surfaces as a requirement for successful vaccination against infectious agents where mucosal immunity is essential. Research efforts, therefore, have been almost universally focused on the induction of mucosal immune responses by providing antigen to and stimulating cells in the local mucosa-draining lymphoid organs.

Biological Response Modifiers

Differentiation of B cells can be effected by cytokines, biologically active polypeptides that serve as means of cellular communication within the organs and tissues of the vertebrate body. The cytokines are a family of biologic response modifiers that also includes the interleukins and the growth factors, such as the various types of transforming growth factor beta ("TGF-β") epidermal growth factor ("EGF"), nerve growth factor ("NGF") and platelet-derived growth factors ("PDGF"). Interleukins are known to play an important role in directing isotype switching and antibody secretion by antigen-activated B cells (Finkelman et al., supra); and TGF-β is essential for expression of the IgA isotype (P. Van Vlasselaer (1992). *J. Immunol.* 148:2062–67; D. Lebman (1990). *Proc. Nat. Acad. Sci. USA* 87:3962–66).

1,25-Dihydroxy Vitamin $D_3$ (1,25(OH)$_2$D$_3$) has been shown to promote the synthesis of biologically active forms of TGF-β in rat cells (D. M. Petkovich et al. (1987). *J. Biol. Chem.* 262:13424–28; J. Pfeilschrifter et al. (1987). *Proc. Nat. Acad. Sci. USA* 84:2024–28).

Mucosal Immunologic Memory

Recently, workers in the field of immunization have generally agreed that long-lasting establishment of an immunologic memory at mucosal surfaces could provide an important means for improving host defense against the load of infectious agents that enter the body through mucosal surfaces. Satisfactory means for establishing a mucosal immunologic immunity has not been obtained.

Systemic immunization can be induced by systemic administration of an antigen, for example, by way of a parenterally administered vaccine, and such systemic immunization can be effective against systemic infection. However, parenterally administered vaccines produce little or no increase in secretory antibody titres at mucosal surfaces.

Direct exposure of the mucosal surface to antigen ("Ag") has been proposed as a means of inducing a mucosal immune response, that is, as a means of producing substantial increases in antigen-specific secretory immunoglobulin A ("sIgA") response, at mucosal surfaces. According to such an approach, the antigen is administered orally (for exposure of gastrointestinal mucosa) or intranasally (for exposure of respiratory mucosa) in quantity sufficient to bathe the mucosal surface. Antigen-specific sIgA responses originating at one mucosal site reportedly disseminate to other mucosally associated lymphoid sites. In one proposed immunization strategy, oral and intranasal vaccines may be useful in improving pulmonary immunization against viral respiratory infections, such as influenza. Over the years, the approach of immunization directly across a mucosal surface has been attempted, using a variety of antigenic substances and a variety of mucosal epithelia as the target (Mestecky et al. (1987), supra).

Most nonviable or noninfectious soluble antigens are poor immunogens when administered intranasally or orally. Establishing mucosal immunologic responses and immunologic memory by exposing a mucosal surface with antigen administered by an oral or intranasal route, therefore, typically requires milligram amounts of antigen for each subject treated, making such an approach exceedingly costly. Various efforts have been made to reduce the quantity of Ag needed to produce the desired response. In one approach, a mucosal adjuvant is administered together with the immunogen for which a mucosal response is desired. For example, Vadjy et al. ((1992). *Immunology* 75:488–92) describes inducing long-term immunological memory to keyhole limpet hemocyanin ("KLH") in the intestinal *lamina propria* of mice by oral priming immunizations with KLH in combination with cholera toxin ("CT") adjuvant. The induced memory responses to KLH in the gut were not reflected in changes in KLH-specific antibody (Ab) titres in serum in these experiments. CT is a known highly potent mucosal immunogen that additionally has an ability to act as a strong mucosal adjuvant to related as well as unrelated antigens; it also is exceedingly toxic. Abraham et al. ((1992). *J Immunol.* 149:3719–26) describes obtaining substantial enhancement of bacterial polysaccharide-specific sIgA response in the lungs of mice, by intranasally administering liposomes containing interleukin-2 ("IL-2"), a cytokine known to augment B cell proliferation and progression to immunoglobulin ("Ig") production, together with bacterial polysaccharide from *Pseudomonas aeruginosa* or *Aerobacter levanicum*; and an enhancement in those mice of resistance to infection. In contrast, there were no significant changes in bacterial polysaccharide-specific Ig in the serum of the mice immunized with liposomes containing both IL-2 and *P. aeruginosa* bacterial polysaccharide. Encapsulation of IL-2 in liposomes was thought to avoid the toxicity that results from high systemic levels of this cytokine.

SUMMARY OF THE INVENTION

The invention relates to a vaccine which comprises an antigen and a lymphoid organ modifying agent. Suitable lymphoid organ modifying agents enhance the production of IL-4, IL-5 or IL-10 in T cells. Such agents include, but are not limited to, 1,25-dihydroxy Vitamin $D_3$ (1,25(OH)$_2$D$_3$), 25-hydroxy Vitamin $D_3$ (25(OH)D$_3$)or biologically active 1,25(OH)$_2$D$_3$ derivatives which are capable of activating the intracellular Vitamin $D_3$ receptor, all trans-retinoic acid, retinoic acid derivatives, retinol and glucocorticoid. The vaccine composition may further comprise an immune response augmenting agent. The immune response augmenting agent enhances production of IL-2, IL-3, IFN-γ or GM-CSF in T cells. Suitable immune response augmenting agents include, but are not limited to, dehydroepiandrosterone (DHEA), DHEA congeners and DHEA-derivatives.

The invention also relates to a method for inducing an antigen-specific mucosal immune response in a subject vertebrate animal which comprises administering a vaccine which comprises an antigen and a lymphoid organ modifying agent to a site which drains into a peripheral lymph compartment. Alternatively, the method comprises separately administering the lymphoid organ modifying agent and a vaccine containing an antigen to the same site. The method may further comprise additionally administering an immune response augmenting agent. The immune response augmenting agent may be administered sequentially or contemporaneously with the lymphoid organ modifying agent.

BRIEF DESCRIPTION OF THE DRAWINGS

FIG. 1A shows release of IL-2.

FIG. 1B shows release of IFN-γ.

FIG. 1C shows release of IL-4.

FIG. 1D shows release of IL-5.

FIG. 1E shows release of IL-10.

FIG. 2A shows the primary serum IgG response.

FIG. 2B shows the primary serum IgA response.

FIG. 2C shows the secondary serum IgG response.

FIG. 2D shows the secondary serum IgA response.

FIG. 3A shows the primary serum IgG response.

FIG. 3B shows the primary serum IgA response.

FIG. 3C shows the secondary serum IgG response.

FIG. 3D shows the secondary serum IgA response.

FIGS. 4A–4D are graphs showing the effect of topically applied $1,25(OH)_2D_3$ on the secretory antibody responses to primary (FIGS. 4A, 4B) and secondary (FIGS. 4C, 4D) subcutaneous immunizations with HibCV in mice. Results from Dt-specific quantitative ELISA for Dt-specific IgG (FIGS. 4A, 4C) and IgA (FIGS. 4B, 4D) are shown for treated mice (data points ●), which received $1,25(OH)_2D_3$ on Day 5 following the primary immunization, and for untreated mice (data points ■), which received no $1,25(OH)_2D_3$.

FIG. 4A shows the primary secretory IgG response.

FIG. 4B shows the primary secretory IgA response.

FIG. 4C shows the secondary secretory IgG response.

FIG. 4D shows the secondary secretory IgA response.

FIGS. 5A–5D are graphs showing the effect of topically applied $1,25(OH)_2D_3$ on the serum antibody responses to primary (FIGS. 5A, 5B) and secondary (FIGS. 5C, 5D) subcutaneous immunizations with HibCV in mice. Results (mean ±S.E.M.) from Hib-specific quantitative ELISA for IgG (FIGS. 5A, 5C) and IgA (FIGS. 5B, 5D) are shown for treated mice (data points ●), which received $1,25(OH)_2D_3$ on Day 5 following the primary immunization, and for untreated mice (data points ■), which received no $1,25(OH)_2D_3$.

FIG. 5A shows the primary serum IgG response.

FIG. 5B shows the primary serum IgA response.

FIG. 5C shows the secondary serum IgG response.

FIG. 5D shows the secondary serum IgA response.

FIGS. 6A–6D are graphs showing the effect of topically applied $1,25(OH)_2D_3$ on the secretory antibody responses to primary (FIGS. 6A, 6B) and secondary (FIGS. 6C, 6D) subcutaneous immunizations with HibCV in mice. Results from Hib-specific quantitative ELISA for IgG (FIGS. 6A, 6C) and IgA (FIGS. 6B, 6D) are shown for treated mice (data points ●), which received $1,25(OH)_2D_3$ on Day 5 following the primary immunization, and for untreated mice (data points ■), which received no $1,25(OH)_2D_3$.

FIG. 6A shows the primary secretory IgG response.

FIG. 6B shows the primary secretory IgA response.

FIG. 6C shows the secondary secretory IgG response.

FIG. 6D shows the secondary secretory IgA response.

FIG. 7A shows the serum IgG response.

FIG. 7B shows the serum IgA response.

FIG. 8A shows lung secretory IgG response.

FIG. 8B shows lung secretory IgA response.

FIG. 8C shows vaginal secretory IgG response.

FIG. 8D shows vaginal secretory IgA response.

FIG. 9A shows the primary mucosal IgA response.

FIG. 9B shows the secondary mucosal IgA response.

FIG. 9C shows the primary mucosal IgG response.

FIG. 9D shows the secondary mucosal IgG response.

FIG. 10A shows the primary serum IgG response.

FIG. 10B shows the secondary serum IgG response.

FIG. 10C shows the primary serum IgA response.

FIG. 10D shows the secondary serum IgA response.

FIGS. 11A and 11B show that IgA production is induced in mucosal tissue with topical administration of $1,25(OH)_2D_3$ five days after administration of vaccine. The IgA responses are shown for mice without $1,25(OH)_2D_3$ treatment (■) and for mice with $1,25(OH)_2D_3$ treatment (●).

FIG. 11A shows the primary mucosal IgA response.

FIG. 11B shows the secondary mucosal IgA response.

FIGS. 11C and 11D shows that IgG production is induced in mucosal tissue with topical administration of $1,25(OH)_2D_3$ five days after administration of vaccine. The IgG responses are shown for mice without $1,25(OH)_2D_3$ treatment (■) and for mice with $1,25(OH)_2D_3$ treatment (●).

FIG. 11C shows the primary mucosal IgG response.

FIG. 11D shows the secondary mucosal IgG response.

FIGS. 13A and 13B show that serum (systemic) antibody response in mature mice following vaccination with Influenza-A Beijing strain is synergistically enhanced by treatment with DHEA and $1,25(OH)_2D_3$. Antibody responses at Day 28 are shown for mice without treatment (■), mice treated with 2 μg DHEA in vaccine (●), mice treated with 0.1 μg $1,25(OH)_2D_3$ in vaccine (▲), and mice treated with 2 μg DHEA and 0.1 μg $1,25(OH)_2D_3$ in vaccine (♦).

FIG. 13A shows the serum IgG response.

FIG. 13B show the serum IgA response.

FIGS. 13C and 13D show that mucosal antibody response in mature mice following vaccination with Influenza-A Beijing strain is synergistically enhanced by treatment with DHEA and $1,25(OH)_2D_3$. Antibody responses at Day 28 are shown for mice without treatment (■), mice treated with 2 μg DHEA in vaccine (●), mice treated with 0.1 μg $1,25(OH)_2D_3$ in vaccine (▲), and mice treated with 2 μg DHEA and 0.1 μg $1,25(OH)_2D_3$ in vaccine (♦).

FIG. 13C shows the mucosal IgG response.

FIG. 13D shows the mucosal IgA response.

FIG. 14A shows the serum IgG response.

FIG. 14B shows the serum IgA response.

FIG. 14C shows the mucosal IgG response.

FIG. 14D shows the mucosal IgA response.

FIG. 15A shows the serum IgG response.

FIG. 15B shows the serum IgA response.

FIG. 15C shows the mucosal IgG response.

FIG. 15D shows the mucosal IgA response.

FIG. 17A shows clinical disease for control plasmid.

FIG. 17B shows clinical disease for gD2 gene containing plasmid.

FIG. 17C shows clinical disease for gD2 gene containing plasmid with $1,25(OH)_2D_3$.

FIG. 21 shows nasal wash neutralizing antibody titres following intranasal challenge with antigen.

DETAILED DESCRIPTION OF THE PREFERRED EMBODIMENTS

Figure 1A:
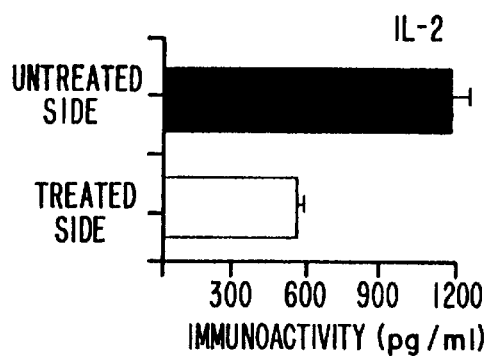
FIGS. 1A–1E are bar graphs showing the effect of topically applied $1,25(OH)_2D_3$ on T cell cytokine production in peripheral lymph nodes in mice. The bars represent the release of the indicated cytokines (IL-2, IFN-γ, IL-4, IL-5 and IL-10) from the lymph node cells isolated from treated and untreated sides of mice in pg/ml.
Figure 1B:
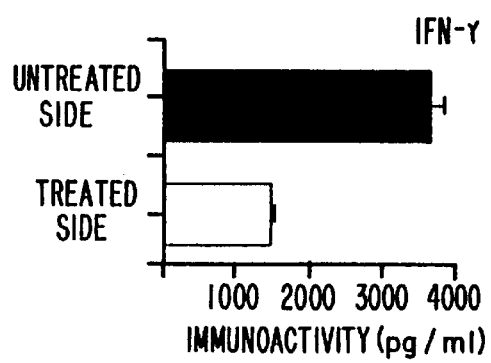
Figure 1C:
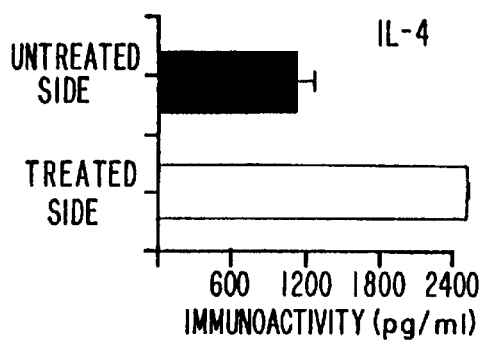
Figure 1D:
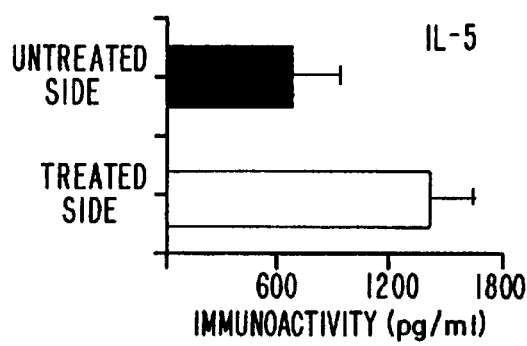
Figure 1E:
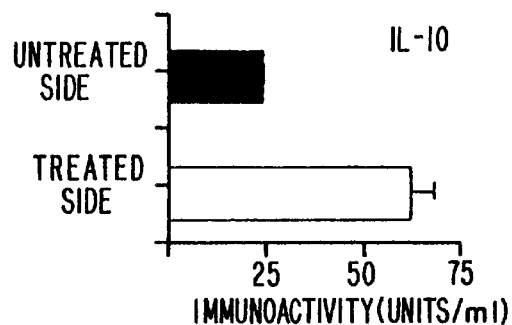
Figure 2A:
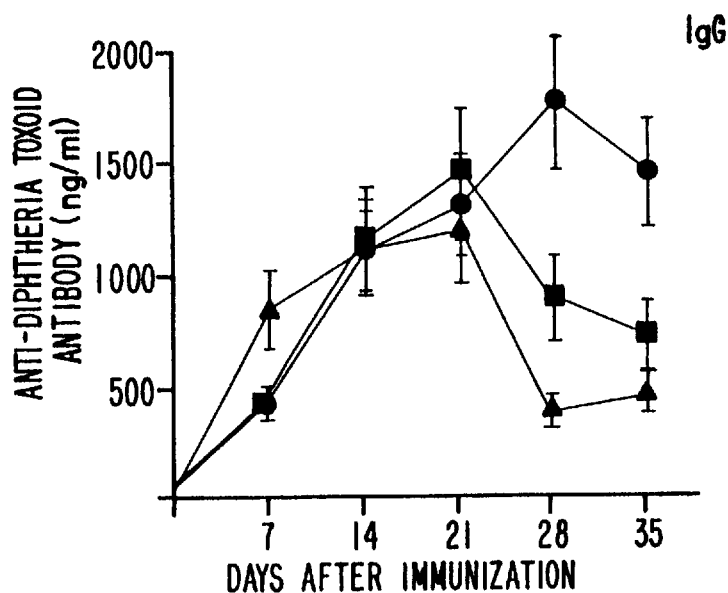
FIGS. 2A–2D are graphs showing the effect of topically applied $1,25(OH)_2D_3$ on the primary (FIGS. 2A, 2B) and secondary (FIGS. 2C, 2D) serum antibody responses to subcutaneous immunizations with Diphtheria toxoid antigen ("Dt") in mice. Results from Dt-specific quantitative ELISA for Dt-specific IgG (FIGS. 2A, 2C) and IgA (FIGS. 2B, 2D) are shown for treated mice that received $1,25(OH)_2D_3$ on Day 0 following primary immunization (data points ●), and for treated mice that received $1,25(OH)_2D_3$ on Day 5 following primary immunization (data points ▲), and for untreated mice (data points ■), which received no $1,25(OH)_2D_3$.
Figure 2B:
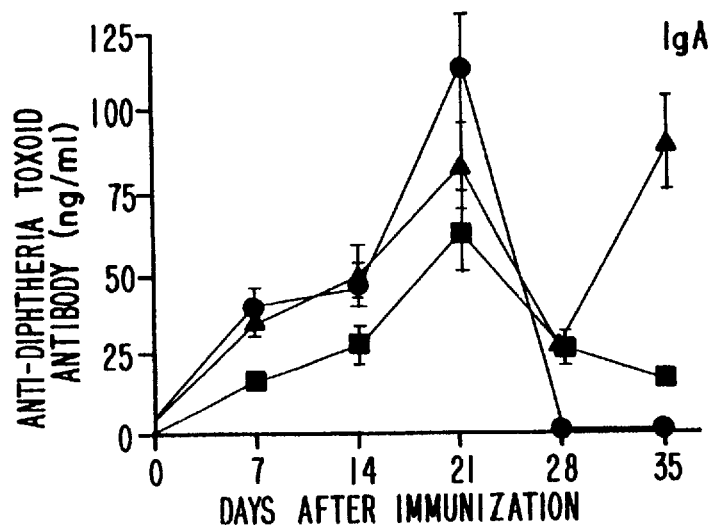
Figure 2C:
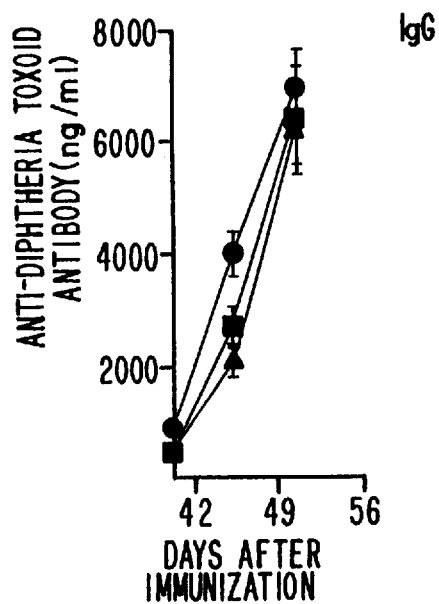
Figure 2D:
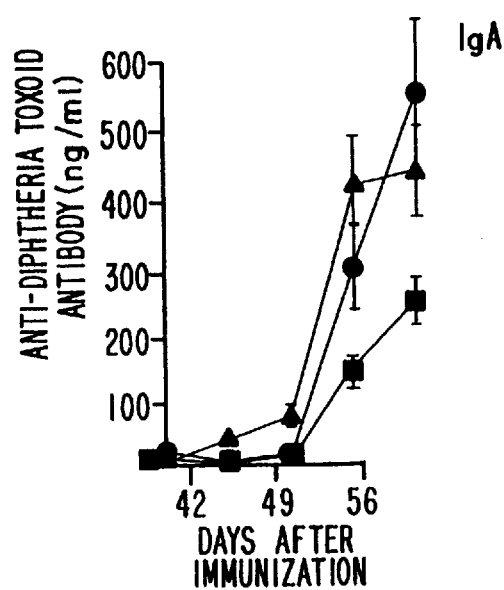
Figure 3A:
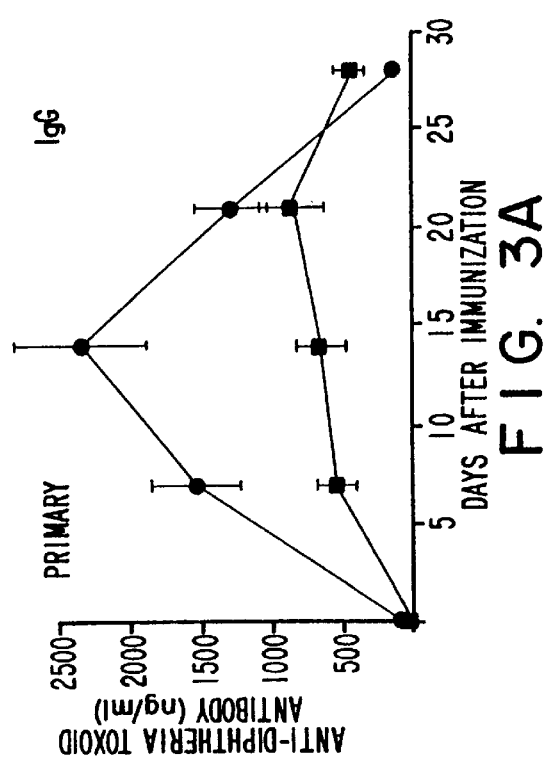
FIGS. 3A–3D are graphs showing the effect of topically applied $1,25(OH)_2D_3$ on the serum antibody responses to primary (FIGS. 3A, 3B) and secondary (FIGS. 3C, 3D) subcutaneous immunizations with a Hemophilus Influenza type b polysaccharide conjugate vaccine ("HibCV"), Hib coupled to Dt, in mice. Results from Dt-specific quantitative ELISA for Dt-specific IgG (FIGS. 3A, 3C) and IgA (FIGS. 3B, 3D) are shown for treated mice (data points ●), which received $1,25(OH)_2D_3$ on Day 5 following the primary immunization, and for untreated mice (data points ■), which received no $1,25(OH)_2D_3$.
Figure 3B:
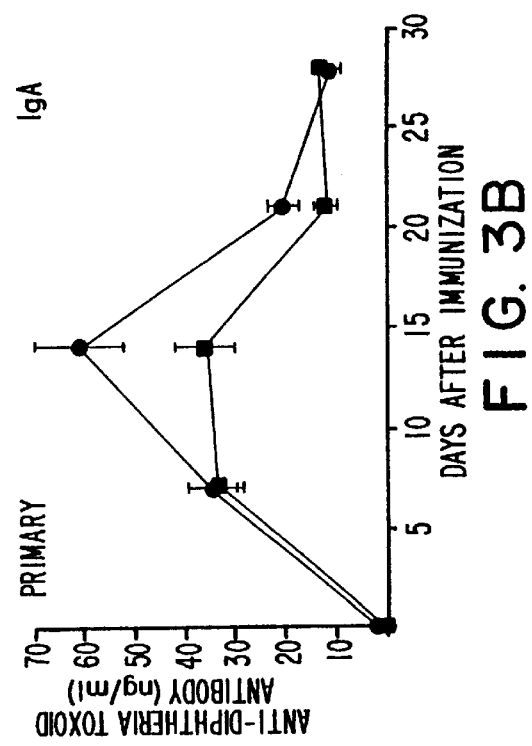
Figure 3C:
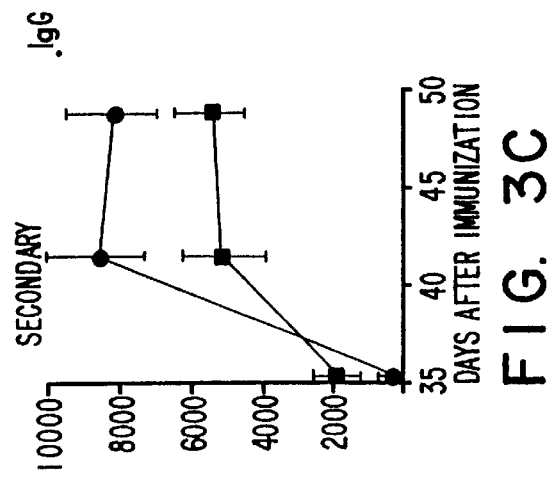
Figure 3D:
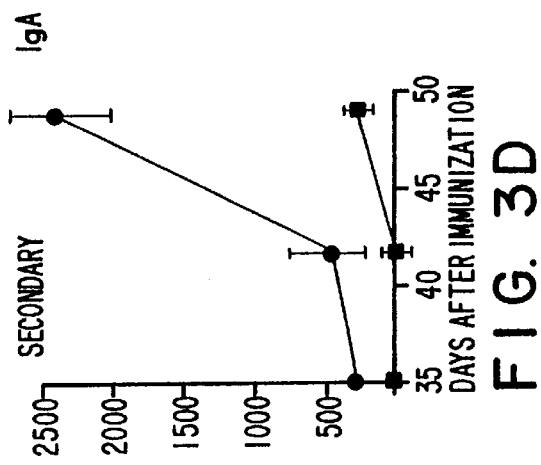

The invention relates to a vaccine which comprises an antigen and a lymphoid organ modifying agent. Suitable lymphoid organ modifying agents enhance the production of IL-4, IL-5 or IL-10 in T cells. Such agents include, but are not limited to, 1,25-dihydroxy Vitamin $D_3$ (1,25$(OH)_2D_3$), 25-hydroxy Vitamin $D_3$ (25$(OH)D_3$) or biologically active 1,2$(OH)_2D_3$ derivatives which are capable of activating the intracellular Vitamin $D_3$ receptor, all transretinoic acid, retinoic acid derivatives, retinol and glucocorticoid. The vaccine composition may further comprise an immune response augmenting agent. The immune response augmenting agent enhances production of IL-2, IL-3, IFN-γ or GM-CSF in T cells. Suitable immune response augmenting agents include, but are not limited to, dehydroepiandrosterone (DHEA), DHEA congeners and DHEA-derivatives.

The invention also relates to a method for inducing an antigen-specific mucosal immune response in a subject vertebrate animal which comprises administering a vaccine which comprises an antigen and a lymphoid organ modifying agent to a site which drains into a peripheral lymph compartment. Alternatively, the method comprises separately administering the lymphoid organ modifying agent and a vaccine containing an antigen to the same site. The method may further comprise additionally administering an immune response augmenting agent. The immune response augmenting agent may be administered sequentially or contemporaneously with the lymphoid organ modifying agent.

Biologic response modifiers, here termed "lymphoid organ modifying agents" have been identified. These biological response modifiers can affect peripheral lymph node T cell function in a manner that mimics the mucosal lymphoid organ microenvironment, and therefore favors induction of an Ag-specific mucosal antibody response as well as Ag-specific serum antibody production in response to antigen administration to sites which drain into the "treated" lymphoid organ.

Particularly, for example, it has been found that topically applied 1,25$(OH)_2D_3$, serving a function as a lymphoid organ modifying agent with appropriately immunized animals, can be used therapeutically to enhance IgA and IgG production in serum as well as to promote secretory antibody production in mucosal secretions.

It has been found that epicutaneous administration of 1,25$(OH)_2D_3$ to animals prior to isolation and in vitro activation of T cells from the draining peripheral lymph node results in emergence in the lymph node T cells of a pattern of cytokines following activation, displaying elevated IL-4, IL-5 and IL-10 production and depressed IL-2 and IFN-γ production. IL-5 and IL-10 are known to synergize with TGF-β to induce differentiation of B cells committed to IgA production (R. Coffman (1989). *J. Exp. Med.* 170:1039–44; T. Defrance et al. (1992). *J. Exp. Med.* 175:671–82). IL-4 has been shown to have a direct influence on B cell isotype switching to the IgGI isotype (Finkelman et al., supra). Once B cells are activated by antigen at the lymph node, both IL-4 and IL-5 can play important roles in stimulating B cells to secrete antibody (J. Purkerson (1992). *J Exp. Med.* 175:973–82).

Moreover, when 1,25$(OH)_2D_3$ is administered to animals prior to in vivo antigen challenge at the peripheral lymph node that drains the site of 1,25$(OH)_2D_3$ administration, an Ag-specific secretory immunologic response in the mucosa can result, as well as an Ag-specific serum immunologic response. Apparently, a result of 1,25$(OH)_2D_3$ and in vivo antigen challenge at the same peripheral lymph node is a "seeding" of the lamina propria with secretory IgA-committed and secretory IgG-committed B cells at sites throughout the mucosa.

In one aspect, in general, the invention features a method for inducing antigen-specific mucosal immunity in a subject vertebrate animal, by administering an effective amount of a lymphoid organ modifying agent to the subject at a site which drains into a peripheral lymphoid organ, and administering an effective amount of the specific antigen to the subject at a site which drains into the same peripheral lymphoid organ. The method further features administering an effective amount of an immune response augmenting agent which enhances T cell lymphokine production, as described in U.S. application Ser. No. 07/779,449, incorporated herein by reference.

The term "individual" as used herein refers to a vertebrate and preferably to a member of a species which naturally produces DHEA and DHEA-S and possesses DHEA-S sulfatase activity, and includes, but is not limited to domestic animals, sports animals and primates, including humans.

An "antigen" refers to a molecule containing one or more epitopes that will stimulate a host's immune system to make a secretory, humoral and/or cellular antigen-specific response, or to a DNA molecule which is capable of producing such an antigen in a vertebrate. The term is also used interchangeably with "immunogen."

The specific antigen can be a protein, a polysaccharide, a lipopolysaccharide or a lipopeptide; or it can be a combination of any of these. Particularly, the specific antigen can include a native protein or protein fragment, or a synthetic protein or protein fragment or peptide; it can include glycoprotein, glycopeptide, lipoprotein, lipopeptide, nucleoprotein, nucleopeptide; it can include a peptide-peptide conjugate; it can include a recombinant nucleic acid expression product. The antigen may further be a DNA molecule which produces an antigen in the vertebrate. Examples of antigens include, but are not limited to, those that are capable of eliciting an immune response against viral or bacterial hepatitis, influenza, diphtheria, tetanus, pertussis, measles, mumps, rubella, polio, pneumococcus, herpes, respiratory syncytial virus, hemophilus influenza type b, chlamydia, varicella-zoster virus or rabies.

"Treatment" refers to the administration to an individual of a composition which yields a protective immune response, and includes prophylaxis and/or therapy.

By "vaccine composition" or "vaccine" is meant an agent used to stimulate the immune system of an individual so that current harm is alleviated, or protection against future harm is provided.

"Immunization" refers to the process of inducing a continuing protective level of antibody and/or cellular immune response which is directed against an antigen to which the organism has been previously exposed.

An "immune response augmenting agent", as used herein, means an agent that is capable, when administered to a vertebrate animal in vivo, of restoring T cell responsiveness to T cell dependent antigens characteristic of normal immune responses to such antigens. Immune response augmenting agents are capable of enhancing T cell production of IL-2, IL-3, IFN-γ or GM-CSF. By way of example, the immune response augmenting agent can be a substance such as DHEA, DHEA congener or a DHEA-derivative (collectively referred to herein as DHEA congener). A DHEA congener is a compound related to DHEA, such as a derivative. Suitable substances can be readily identified by screening for enhanced IL-2, IL-3, IFN-γ or GM-CSF production by T cells as described in Ser. No. 07/779,499.

Examples of "DHEA", "DHEA congener" or "DHEA-derivative", include but are not limited to, compounds having the formula

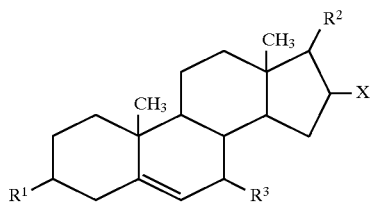

wherein

X is H or halogen;

$R^1$, $R^2$ and $R^3$ are independently =O, —OH, —SH, H, halogen, pharmaceutically acceptable ester, pharmaceutically acceptable thioester, pharmaceutically acceptable ether, pharmaceutically acceptable thioether, pharmaceutically acceptable inorganic esters, pharmaceutically acceptable monosaccharide, disaccharide or oligosaccharide, spirooxirane, spirothirane, —OSO$_2$R$^5$ or —OPOR$^5$R$^6$;

$R^5$ and $R^6$ are independently —OH, pharmaceutically acceptable esters or pharmaceutically acceptable ethers; and pharmaceutically acceptable salts.

Thus, examples of suitable DHEA congeners include compounds in which:

(1) $R^2$ is =O, $R^3$ and X are each H and $R^1$ is =O, —OH, pharmaceutically acceptable esters thereof, pharmaceutically acceptable ethers thereof or pharmaceutically acceptable salts;

(2) $R^2$ is =O, $R^3$ is H, X is halogen and $R^1$ is =O, —OH, pharmaceutically acceptable esters thereof, pharmaceutically acceptable ethers thereof or pharmaceutically acceptable salts;

(3) $R^2$ is =O, $R^3$ and X are each H and $R^1$ is —SH, pharmaceutically acceptable thioesters thereof, pharmaceutically acceptable thioethers thereof or pharmaceutically acceptable salts;

(4) $R^2$ is =O, $R^3$ is H, X is halogen and $R^1$ is —SH, pharmaceutically acceptable thioesters thereof, pharmaceutically acceptable thioethers thereof or pharmaceutically acceptable salts;

(5) $R^2$ is =O, X is H and $R^1$ and $R^3$ are independently =O, —OH, pharmaceutically acceptable esters thereof, pharmaceutically acceptable ethers thereof or pharmaceutically acceptable salts;

(6) $R^2$ is =O, X is halogen and $R^1$ and $R^3$ are independently =O, —OH, pharmaceutically acceptable esters thereof, pharmaceutically acceptable ethers thereof or pharmaceutically acceptable salts;

(7) $R^2$ is =O, X is H and $R^1$ and $R^3$ are independently —SH, pharmaceutically acceptable thioesters thereof, pharmaceutically acceptable thioethers thereof or pharmaceutically acceptable salts;

(8) $R^2$ is =O, X is halogen and $R^1$ and $R^3$ are independently —SH, pharmaceutically acceptable thioesters thereof, pharmaceutically acceptable thioethers thereof or pharmaceutically acceptable salts;

(9) $R^2$ is —OH, $R^3$ and X are each H and $R^1$ is =O, —OH, pharmaceutically acceptable esters thereof, pharmaceutically acceptable ethers thereof or pharmaceutically acceptable salts;

(10) $R^2$ is —OH, $R^3$ is H, X is halogen and $R^1$ is =O, —OH, pharmaceutically acceptable esters thereof, pharmaceutically acceptable ethers thereof or pharmaceutically acceptable salts;

(11) $R^2$ is —OH, $R^3$ and X are each H and $R^1$ is —SH, pharmaceutically acceptable thioesters thereof, pharmaceutically acceptable thioethers thereof or pharmaceutically acceptable salts;

(12) $R^2$ is —OH, R is H, X is halogen and $R^1$ is —SH, pharmaceutically acceptable thioesters thereof, pharmaceutically acceptable thioethers thereof or pharmaceutically acceptable salts;

(13) $R^2$ is —OH, X is H and $R^1$ and $R^3$ are independently =O, —OH, pharmaceutically acceptable esters thereof, pharmaceutically acceptable ethers thereof or pharmaceutically acceptable salts;

(14) $R^2$ is —OH, X is halogen and $R^1$ and $R^3$ are independently =O, —OH, pharmaceutically acceptable esters thereof, pharmaceutically acceptable ethers thereof or pharmaceutically acceptable salts;

(15) $R^2$ is —OH, X is H and $R^1$ and $R^3$ are independently —SH, pharmaceutically acceptable thioesters thereof, pharmaceutically acceptable thioethers thereof or pharmaceutically acceptable salts;

(16) $R^2$ is —OH, X is halogen and $R^1$ and $R^3$ are independently —SH, pharmaceutically acceptable thioesters thereof, pharmaceutically acceptable thioethers thereof or pharmaceutically acceptable salts;

(17) $R^2$ is —SH, $R^3$ and X are each H and $R^1$ is =O, —OH, pharmaceutically acceptable esters thereof, pharmaceutically acceptable ethers thereof or pharmaceutically acceptable salts;

(18) $R^2$ is —SH, $R^3$ is H, X is halogen and $R^1$ is =0, —OH, pharmaceutically acceptable esters thereof, pharmaceutically acceptable ethers thereof or pharmaceutically acceptable salts;

(19) $R^2$ is —SH, $R^3$ and X are each H and $R^1$ is —SH, pharmaceutically acceptable thioesters thereof, pharmaceutically acceptable thioethers thereof or pharmaceutically acceptable salts;

(20) $R^2$ is —SH, $R^3$ is H, X is halogen and $R^1$ is —SH, pharmaceutically acceptable thioesters thereof, pharmaceutically acceptable thioethers thereof or pharmaceutically acceptable salts;

(21) $R^2$ is —SH, X is H and $R^1$ and $R^3$ are independently =O, —OH, pharmaceutically acceptable esters thereof, pharmaceutically acceptable ethers thereof or pharmaceutically acceptable salts;

(22) $R^2$ is —SH, X is halogen and $R^1$ and $R^3$ are independently =O, —OH, pharmaceutically acceptable esters thereof, pharmaceutically acceptable ethers thereof or pharmaceutically acceptable salts;

(23) $R^2$ is —SH, X is H and $R^1$ and $R^3$ are independently —SH, pharmaceutically acceptable thioesters thereof, pharmaceutically acceptable thioethers thereof or pharmaceutically acceptable salts;

(24) $R^2$ is —SH, X is halogen and $R^1$ and $R^3$ are independently —SH, pharmaceutically acceptable thioesters thereof, pharmaceutically acceptable thioethers thereof or pharmaceutically acceptable salts;

(25) X is H and $R^1$, $R^2$ and $R^3$ are independently =O, —OH, a sugar residue, pharmaceutically acceptable esters thereof, pharmaceutically acceptable ethers thereof or pharmaceutically acceptable salts, wherein at least one of $R^1$, $R^2$ and $R^3$ is a sugar residue;

(26) X is halogen and $R^1$, $R^2$ and $R^3$ are independently =O, —OH, a sugar residue, pharmaceutically acceptable esters thereof, pharmaceutically acceptable ethers thereof or pharmaceutically acceptable salts, wherein at least one of $R^1$, $R^2$ and $R^3$ is a sugar residue;

(27) X is H and $R^1$, $R^2$ and $R^3$ are independently =O, —OH, pharmaceutically acceptable inorganic esters thereof or pharmaceutically acceptable salts, wherein at least one of $R^1$, $R^2$ and $R^3$ is an inorganic ester;

(28) X is halogen and $R^1$, $R^2$ and $R^3$ are independently =O, —OH, pharmaceutically acceptable inorganic esters thereof or pharmaceutically acceptable salts, wherein at least one of $R^1$, $R^2$ and $R^3$ is an inorganic ester.

Pharmaceutically acceptable esters or thioesters include, but are not limited to, esters or thioesters of the formula —OOCR or —SOCR, wherein R is a pharmaceutically acceptable alkyl, alkenyl, aryl, alkylaryl, arylalkyl, spingosine or substituted spingolipid groups, such as propionate, enanthate, cypionate, succinate, decanoate and phenylpropionate esters.

Pharmaceutically acceptable ethers or thioethers include, but are not limited to, ethers or thioethers of the formula —OR or —SR, wherein R is as defined above or enol, or —$OR^4$ is an unsubstituted or substituted spirooxirane or —SR is a spirothiane.

Suitable sugar residues include, but are not limited to monosaccharides, disaccharides and oligosaccharides, such as a glucuronate.

Pharmaceutically acceptable inorganic esters include, but are not limited to, inorganic esters of the formula —$OSO_2R^5$ or —$OPOR^5R^6$, wherein $R^5$ and $R^6$ are independently —OH, pharmaceutically acceptable esters, pharmaceutically acceptable ethers or pharmaceutically acceptable salts.

"Lymphoid organ modifying agent", as used herein, means a modifier that is capable, when administered to a vertebrate animal in vivo at a peripheral site, of altering the microenvironment of a peripheral lymphoid organ that drains from the administration site, such that activated lymphocytes and macrophages residing within the lymphoid organ exhibit a pattern of cytokines more typical of the microenvironment of a lymphoid organ of the mucosal lymphoid compartment. Particularly, a pattern of cytokines more typical of a mucosal lymphoid organ is characterized by relatively enhanced production of one or more of active TGF-β, IL-4, IL-5, and IL-10, and relatively decreased production (or at least no relatively enhanced production) of one or more of IL-2 and IFN-γ. In preferred embodiments, the lymphoid organ modifying agent includes a biological response modifier that can, or a combination of biological response modifiers that together can, when administered to a peripheral lymph organ, result in the lymphoid organ exhibiting a pattern of cytokines more typical of a mucosal lymphoid organ. By way of example, it can be a substance known to enhance or facilitate production of active TGF-β, such as, for example, retinoic acid, retinoic acid derivatives, retinol or retinol derivatives; or it can be 1,25$(OH)_2D_3$, 25$(OH)D_3$ or biologically active 1,25$(OH)_2D_3$ derivatives; or glucocorticoids. Biologically active 1,25$(OH)_2D_3$ derivatives are those derivatives which are capable of activating the intracellular Vitamin $D_3$ receptor. Suitable derivatives can thus be readily identified by screening for activation of the intracellular Vitamin $D_3$ receptor (Minghetti and Norman (1988). *FASEB J.* 2:3043–3053). Alternatively, suitable derivatives can be readily identified by screening for enhanced IL-4 production by T cells as described in Ser. No. 07/779,499. Examples of suitable biologically active Vitamin $D_3$ derivatives include, but are not limited to, 1,25dihydroxy-16-ene Vitamin $D_3$ and calcipotriene. Preferably, the lymphoid organ modifying agent is administered epicutaneously at a peripheral anatomical site (such as, for human subjects, for example, the arm or buttocks or leg); and the specific antigen is administered to the same anatomical site, or to a site known to drain into the same lymphoid organ that receives drainage from the site of administration of the lymphoid organ modifying agent. In one mode of administration, the lymphoid organ modifying agent can be combined with the specific antigen for simultaneous administration at the same site. The lymphoid organ modifying agent and the specific antigen, or both of them, can be administered by injection.

The lymphoid organ modifying agent can be administered at a time concurrent with, prior to, or following the time of administration of the specific antigen. The specific antigen and the lymphoid organ modifying agent can be combined prior to administration and administered together, or they can be administered sequentially. When the lymphoid organ modifying agent is administered prior to the administration of the specific antigen, it is administered 0.1 to 24 hours, preferably 0.1 to 6 hours before the antigen. When the lymphoid organ modifying agent is administered after the administration of the specific antigen, it is administered 0.1 hour to 6 days, preferably 0.1 hour to 5 days, and most preferably 2 to 3 days after the antigen.

Preferably, however, the lymphoid organ modifying agent is administered concurrently with the specific antigen, or still more preferably, at a time following administration of the specific antigen. Administration of the specific antigen results initially in a clonal expansion (proliferation) of T cells and B cells in the lymphoid organ that drains the site of administration, and for a time the cells are sequestered in the lymphoid organ; thereafter, the cells are dispatched to the general circulation. Thus, the lymphoid organ modifying agent also facilitates B cell homing to mucosal tissues and the generation of mucosal immune responses at all mucosal sites. In particular, therefore, it can be preferable to administer the lymphoid organ modifying agent at a time after primary immunization when the resulting proliferation of T cells and B cells is well developed, and while, for the most part, the antigen-activated cells remain sequestered in the lymphoid organ. Generally, the proliferation of T cells and B cells can be expected to be well developed within about two or three days following primary immunization with the specific antigen; and substantial movement of the cells into the general circulation can be expected about five days following primary immunization, or somewhat later.

It may be particularly preferred that the lymphoid organ modifying agent reach the draining lymphoid organ at a time following primary immunization with the specific antigen but before a substantial portion of the resulting expanded B cell and T cell populations have moved into the general circulation. This can be accomplished, for example, by first administering the antigen, and thereafter (preferably at least about two or three days thereafter, but not more than about five days thereafter) administering the lymphoid organ modifying agent. Or this can be accomplished by compounding the lymphoid organ modifying agent with means for delaying its release following administration, and then combining the delayed-release compounded lymphoid organ modifying agent with the specific antigen in a composition for simultaneous administration. Means for delayed release are well-known, and the chemistry or the structure of the means can be adjusted to provide a suitable time period for the delay. Encapsulation of the lymphoid organ modifying agent within liposomes, or within a biodegradable matrix, for example, can effect a delay in delivery of the lymphoid organ modifying agent (relative to the delivery of the antigen) from the administration site to the lymphoid organ.

An "effective amount" of lymphoid organ modifying agent is a quantity of administered lymphoid organ modifying agent that is able to alter, qualitatively, the types of cytokines and growth factors capable of being produced by activated cells residing in a draining lymphoid organ, with the result that representative species produced in the altered lymphoid organ include one or more of active TGF-β, IL-10, IL-4, and IL-5. For epicutaneous application of the lymphoid organ modifying agent, amounts can be in the range of about 0.1–500 μg, preferably 0.5–250 μg, for a human subject, or in the range of about 0.01–5.0 μg/kg body weight of the subject animal. Effective amounts for subcutaneous, intramuscular or intracutaneous administration may vary to some degree, but can be in the same general range as for epicutaneous application.

An effective amount of antigen is an amount that is the same as that amount which is capable, when administered without a lymphoid organ modifier, of eliciting a demonstrable humoral immune response. For many antigens, this is in the range of about 5–100 μg for a human subject. The appropriate amount of antigen to be used is dependent on the specific antigen and is well known in the art.

An effective amount of an immune response augmenting agent is an amount that restores T cell responsiveness in an immunodeficient individual, such as an immunodeficiency resulting from age or stress. The amount of immune response augmenting agent may be in the range of about 10–1,000 μg, preferably 10–900 μg, more preferably 10–500 μg, and most preferably 20–200 μg, for a human subject, or in the range of about 0.2–10 μg/kg body weight of the subject animal, if administered by injection If administered orally, the amount may range from 10–100 mg/day, preferably 20–50 μg/day for a human subject, or in the range of about 0.5–5 mg/kg/day for an animal subject.

The immune response augmenting agent can be administered at a time concurrent with, prior to or following the time of administration of the lymphoid organ modifying agent. The immune response augmenting agent and the lymphoid organ modifying agent can be combined prior to administration of both agents can be combined with the specific antigen prior to administration. When the immune response augmenting agent is administered prior to the administration of the lymphoid organ modifying agent, it is administered 0.1 hr. to 14 days, preferably 0.1 hr to 5 days before the lymphoid organ modifying agent. When the immune response augmenting agent is administered after the administration of the lymphoid organ modifying agent, it is administered 0.1 to 24 hrs, preferably 0.1 to 6 hrs after the lymphoid organ modifying agent. It is preferred that the immune response augmenting agent be administered prior to the lymphoid organ modifying agent. When the immune response augmenting agent is administered prior to the lymphoid organ modifying agent, the immune response augmenting agent is preferably DHEA-S. It is preferred to concurrently administer the lymphoid organ modifying agent and the specific antigen in this embodiment.

In another general aspect, the invention features a composition for inducing an antigen-specific mucosal immune response, including a lymphoid organ modifying agent and a specific antigen in a pharmaceutically acceptable carrier. The composition may further include an immune response augmenting agent. In preferred embodiments, the lymphoid organ modifying agent includes one or more of $1,25(OH)_2D_3$, or a retinoid such as all trans-retinoic acid. Biologically active Vitamin $D_3$ derivatives which are capable of activating the intracellular Vitamin $D_3$ receptor, glucocorticoid and retinoic acid derivatives, retinol and retinol derivatives, can also be used as lymphoid organ modifying agents. The immune response augmenting agent includes one or more DHEA or DHEA derivative. It has been found that a synergistic effect on the immune response is achieved when the composition includes at least one lymphoid organ modifying agent and at least one immune response augmenting agent. In some preferred embodiments, the lymphoid organ modifying agent in the composition is compounded with means for delaying its release following administration, such as encapsulation in a liposome or a biodegradable matrix, so that the movement of the lymphoid organ modifying agent from the delivery site to the draining lymphoid organ is delayed relative to that of the antigen.

Because the method of the invention can result in a common mucosal immune response, secretion of antigen-specific immunoglobulins will occur at all mucosal surfaces. A lactating mammal that has been treated according to the invention will produce antigen-specific immunoglobulins in the secretions of the mammary glands. A female mammal that is treated according to the invention during pregnancy, or treated prior to pregnancy and then rechallenged with the specific antigen during pregnancy, will produce antigen-specific immunoglobulins in the colostrum and in the milk. This provides a means for generating a specific mucosal immune response in the female mammal, without infecting the mother, and then transferring a specific passive immunity from the female mammal to the suckling newborn or infant.

Thus, in another general aspect, the invention features a method for inducing production of antigen-specific antibodies in the mammary secretions of a female mammal, by administering an effective amount of a lymphoid organ modifying agent to the female mammal at a site which drains into a peripheral lymphoid organ, and administering an effective amount of the specific antigen to the female mammal at a site which drains into the same peripheral lymphoid organ. And in another general aspect, the invention features a method for conferring a specific passive immunity to a suckling mammal, by permitting the suckling mammal to consume mammary secretions from a female so treated.

The invention can be used for immunization of any vertebrate animal, and is particularly useful in inducing an antigen-specific mucosal immune response in a human subject.

According to the invention, the lymphoid organ modifying agent can be administered before the specific antigen is administered, after the specific antigen is administered or concurrently with the antigen; or the antigen and the lymphoid organ modifying agent can be administered at least partly concurrently.

The antigen can be administered to the animal in a manner, and in an amount, suitable for inducing a demonstrable humoral response to the antigen in the animal. The antigen can be applied epicutaneously, for transdermal administration, or it can be administered by injection or infusion, subcutaneously, intramuscularly or intradermally.

The lymphoid organ modifying agents can be formulated for a variety of modes of administration, including systemic and topical or localized administration. Techniques and formulations generally may be found in *Remington's Pharmaceutical Sciences*, Mack Publishing Co., Easton, Pa., latest edition. An effective amount of lymphoid organ modifying agent can vary according to the mode of administration and according to the kind of animal being treated. In general, an effect amount will range from about 0.01–1.0 μg lymphoid organ modifying agent/kg body weight, or from about 0.1–500 μg, preferably 0.1–400 μg, and more preferably 0.5–250 μg, for human subjects.

According to the invention, the lymphoid organ modifying agent and the antigen are applied at the same site, or at sites which drain into the same peripheral lymphoid compartment. Anatomical location of such sites is well known.

The lymphoid organ modifying agent can be applied epicutaneously for transdermal administration. Penetrants appropriate to the dermal barrier can be used in the formulation. The lymphoid organ modifying agent can be formulated into ointments, salves, gels or creams, as is generally known in the art.

Alternatively, the lymphoid organ modifying agent can be administered by a subcutaneous, intramuscular or intradermal route, as by injection or infusion. For injection, the lymphoid organ modifying agent of the invention can be formulated in liquid solutions, preferably in physiologically compatible buffers such as Hank's solution or Ringer's solution. In addition, the lymphoid organ modifying agent may be formulated in solid form and redissolved or suspended immediately prior to use.

It has been found that the immune system should be functioning as that of a normal mature adult in order for the lymphoid organ modifying agent to induce a mucosal immune response. If the immune system is not fully competent or the individual is otherwise immunologically deficient, such as results in the very young, the aged, individuals under stress, or the like (see, e.g., U.S. application Ser. No. 07/779,499), it may be necessary to augment the immune system for proper functioning of the lymphoid organ modifying agent. The immune system is augmented by administering an immune response augmenting agent, as described in U.S. application Ser. No. 07/779,449, U.S. application Ser. No. 08/123,843 and U.S. application Ser. No. 08/487,173 filed concurrently herewith (attorney docket number 23691-108469-1), each of which are incorporated herein by reference. The immune response augmenting agent is preferably administered for 0.1 hr to 14 days, preferably 0.1 hr to 5 days prior to the administration of the lymphoid organ modifying agent and the administration of the specific antigen.

The immune response augmenting agent may be administered prior to, or contemporaneously with, or after the lymphoid organ modifying agent. It can be administered by an epicutaneous, subcutaneous, intramuscular or interdermal route, as by injection or infusion, or it can be administered orally. Alternatively, the individual may be treated with the immune response augmenting agent before induction of the mucosal immune response described above. The immune response augmenting agent may be formulated as described above. In general, an effective amount of immune response augmenting agent may be about 10–1,000 μg, preferably 10–900 μg, more preferably 10–500 μg, most preferably 20–200 μg, for a human subject, if administered by injection. If administered orally, an effective amount of immune response augmenting agent may be about 10–100 mg/day, preferably 20–50 mg/day. The immune response augmenting agent can be administered orally for one to three weeks prior to or after vaccination, or longer, as necessary.

Described below are examples of the present invention which are provided only for illustrative purposes, and not to limit the scope of the present invention. In light of the present disclosure, numerous embodiments within the scope of the claims will be apparent to those of ordinary skill in the art.

EXAMPLE 1

Materials and Methods

Mice. Female C3H/HeN MTV$^-$ mice were bred and housed in the University of Utah Vivarium from breeding stock originally purchased from the National Cancer Institute. In each experiment, groups of three to five age-matched mice were used.

Antibodies. Monoclonal antibody reagents used in the present study were prepared from culture supernatants of appropriate B cell hybridomas adapted to growth under serum-free conditions. The hybridoma clones secreting rat anti-murine IL-2 (S4B6), and rat anti-γIFN (XMG1.2) were obtained from DNAX (Palo Alto, Calif.). Hybridoma cell clones producing rat antibody specific for murine IL-4 (11B11), or murine IFN-γ (R46A2) were purchased from the ATCC. Purified anti-cytokine antibodies were then used for quantification of murine cytokines in culture supernatants by capture ELISA. Additionally, the following rat anti-murine cytokine antibodies were obtained from PharMingen (San Diego, Calif.) and then used for quantification of specific murine cytokines by capture ELISA: biotinylated anti-IL-4 (BVD6-24G2) and anti-murine IL-10 antibodies (Cat. nos. 18141 and 18152), and a set of two rat anti-murine IL-2 monoclonal antibodies.

Biological Response Modifiers. Murine recombinant IL-2, IL-4, IL-5, and IFN-γ were obtained from Genzyme (Cambridge, Mass.) and used as a reference in monospecific ELISA assays. In addition, murine recombinant IL-2, IL-4, and IL-5 were derived from culture supernatants of X63Ag8-653 cells transfected with multiple copies of a single murine interleukin gene. After the relative concentration of each lymphokine in culture supernatants was determined by a comparison to a known recombinant standard, these reagents were used as reference lymphokines in appropriate assays. The IL-10 standard was obtained from PharMingen. 1,25(OH)$_2$D$_3$ was received by request from Milan Uskokovic (Hoffman-LaRoche, Nutley, N.J.), dissolved in 95% ethanol as a stock solution of 10$^{-3}$M and then stored at −20° C. For topical use, 1–2 μg of 1,25(OH)$_2$D$_3$ was administered in ethanol to the same site as the site of immunization, the dorsal surface of the hind footpad.

Capture ELISA Assays for Quantitative Lymphokine Determination. Where indicated, the amounts of lymphokine in test supernatants were measured by a capture ELISA. Briefly, 100 μl of an appropriate capture monoclonal antibody is added to the wells of a 96-well microtest plate (Corning #2581) at a concentration of 1–2 μg/ml in 0.5M Tris-HCl (pH 9.6). Following extensive washing and the blocking of reactive sites on the plastic with PBS/10% FCS, test supernatants and two-fold serial dilutions of a reference lymphokine (100 μl/well) were dispensed. After sufficient incubation and washing, 100 ml of the biotinylated detecting antibody, 1–2 μg/ml, was dispensed into each well. The ELISA was developed, after extensive further washing, using avidin conjugated to horseradish peroxidase and ABTS-substrate. O.D. readings were performed at 405 nM using a Vmax 96-well microtest plate spectrophotometer (Molecular Devices, Menlo Park, Calif.). Results of the analysis of each cytokine are reported in pg/ml±SD.

Antibody Responses. Purified Diphtheria toxoid (Dt) was received as a gift from Connaught Laboratories (London, Ont., Canada). An antibody response to Dt was elicited from mice following a single footpad injection of 10 μg purified protein delivered in a 25 μl volume of aluminum hydroxide (273 μg/ml). Hemophilus Influenza type b conjugate vaccine (HibCV) used for immunization, consisting of Hib polysaccharide chemically coupled to Diphtheria toxoid, was purchased at the University of Utah hospital pharmacy. 500 ng of H. Influenza type b polysaccharide (HibCV) coupled to 1 mg of diphtheria toxoid was used as the dose of immunogen. This immunogen was delivered in a 25 μl volume of aluminum hydroxide (273 μg/ml). Quantification of specific antibody in a serum sample was performed using an indirect ELISA method, with reagents purchased from Southern Biotechnology Associates (Birmingham, Ala.) and Zymed Laboratories, Inc. (San Francisco, Calif.). For detection of Diphtheria toxoid-specific antibodies, purified Dt was diluted in 0.05M Tris-HCl (pH 9.6) at a concentration of 2.0 μg/ml and then dispensed into 96-well plates. For detection of Hib-specific antibodies, 100 μl of a Hib-meningococcal protein conjugate, at a dilution to 200 ng/ml polysaccharide in 0.05M Tris-HCl (pH 9.6) was dispensed into 96-well plates. Following incubation for a minimum of two hours at room temperature or overnight at 4° C., all plates were blocked with PBS-0.05% Tween 20/1.0% bovine serum albumin (BSA) for an additional two-hour incubation at room temperature. Prior to adding the test samples, the plates were washed free of blocking buffer using three washes of distilled water and one wash with PBS/0.05% Tween 20. Individual samples were first diluted in PBS 0.05% Tween 20/1.0% BSA, and then 100 μl was dispensed into appropriate wells of the antigen-coated plates. Included on each plate was an Ig standard: a series of two-fold dilutions of either purified IgG (all subclasses) or IgA (reference standards). The reference Ig were captured by goat anti-murine Ig, which is known to bind all murine Ig isotypes. These plates were incubated at room temperature overnight, followed by 3x wash in distilled water and one wash in PBS/0.05% Tween 20. The detection antibody (HRP-linked goat anti-mouse Ig specific for IgG and IgA) was diluted in PBS/Tween/10% normal goat serum at a dilution recommended by the manufacturer. After a final incubation and wash series the ELISA was developed using ABTS-substrate. O.D. readings were recorded at 405 nM using a Vmax 96-well microtest plate spectrophotometer (Molecular Devices, Menlo Park, Calif.). A simple linear regression analysis of the Ig titration generated a reference curve for calculating the amount of specific antibody contained in the test samples. Data are reported as ng/ml±SEM.

EXAMPLE 2

Administration of 1,25(OH)$_2$D$_3$ Alters Cytokine Production in Peripheral Lymphoid Organs To demonstrate the lymphoid organ modifying effect of 1,25(OH)$_2$D$_3$ in the mouse, i.e., its effect on the pattern of cytokine production in peripheral lymphoid organs, 1,25 (OH)$_2$D$_3$ was topically administered to the right front paw (the treated side) and an ethanol vehicle was topically administered to the left front paw of each mouse. After three hours, mice were sacrificed and lymph node cells from the draining lymph nodes from both the treated and untreated sides of experimental mice were removed, and the resident cells were dissociated and activated in vitro using 1 μg/ml anti CD$_3$ε to stimulate cytokine production. Culture supernatants were harvested after 24 hours and were then assayed for individual cytokines using monospecific capture ELISAs. The results are shown in FIGS. 1A–1E, in which the bars represent the release of the indicated cytokines (IL-2, IFN-γ, IL-4, IL-5 and IL-10) from the lymph node cells isolated from treated and untreated sides of mice in pg/ml. The results indicate that epicutaneous in vivo treatment of mice with 2 μg of 1,25(OH)$_2$D$_3$ is sufficient to mediate alterations in the patterns of cytokines produced by activated T cells in the draining lymph node, with IL-2 and IFN-γ being inhibited and IL-4, IL-5 and IL-10 being enhanced.

EXAMPLE 3

Administration of 1,25(OH)$_2$D$_3$ Enhances Production of IgA in Serum

In a first demonstration of the effect of epicutaneous 1,25(OH)$_2$D$_3$ administration on immune response to a specific antigen in the mouse, C3H/HeN female mice were given a primary immunization subcutaneously in the right footpad with 10 μg Dt in aluminum hydroxide prepared and delivered as set out in Example 1. Two distinct subsets of these mice ("treated mice") were administered 2 μg 1,25 (OH)$_2$D$_3$ epicutaneously to the right footpad surface on Day 0 and at Day 5 after immunization. The remaining mice ("untreated mice") received an equal volume of the ethanol carrier. After weekly sampling of serum, mice were secondarily immunized subcutaneously through an intrapelvic route with Dt and no additional exposure to 1,25(OH)$_2$D$_3$. Serum samples from the treated and untreated groups of mice were collected and all primary and secondary samples were then assayed individually using a Dt-specific, quantitative ELISA for IgG and IgA. The results are shown in FIGS. 2A–2D, in which the mean anti-Diphtheria toxoid antibody response (ng/ml) for each group of mice is presented graphically. The results demonstrate that IgG response to a protein antigen predominates in the serum of Dt-immune mice. The IgA response, a much weaker constituent of the response to Dt in the serum, was substantially enhanced by treatment of mice with 1,25(OH)$_2$D$_3$. These elevations persisted post-secondary immunization as well, even though no additional hormone treatment was given at the time of secondary antigen administration.

EXAMPLE 4

Administration of 1,25(OH)$_2$D$_3$ Induces Immunoglobulin Production in Serum and Mucosal Tissue In a further demonstration, groups of C3H/HeN female mice were administered a primary immunization with the Hemophilus Influenza type b polysaccharide conjugate vaccine, Hib coupled to Dt (HibCV). A subset of these mice were treated epicutaneously with 2 μg 1,25(OH)$_2$D$_3$ on Day 5 at the same site of immunization. Serum samples and vaginal washings were collected weekly during the primary response and all samples were then assayed individually using Dt-specific and Hib-specific quantitative ELISA for the IgG and IgA isotypes. The results for each immunization regiment are shown in FIGS. 3A–3D (Dt [i.e., protein component] specific serum antibodies); 4A–4D (Dt specific secretory antibodies); 5A–5D (Hib [i.e., polysaccharide component] specific serum antibodies), and 6A–6D (Hib [i.e., polysaccharide component] specific secretory antibodies), in which the quantity of antibody produced (mean±SEM) as a result is presented graphically. The results show that the IgA and IgG responses to both the protein and the polysaccharide components of the HibCV in both serum and vaginal secretions was enhanced when the immunized mice were treated with a small amount of $1,25(OH)_2D_3$ five days after immunization. Most notably, the concentration of detectable IgA and IgG specific for both the polysaccharide and the proteins moieties of the vaccine in vaginal secretions changed. Moreover, the polysaccharide component of the HibCV stimulated an IgA response in the serum that was as strong as the IgG response, and stronger than the IgG response in the secretions. Thus, IgA appears to represent a dominant isotype in the antibody response to Hib polysaccharide.

Topical administration of $1,25(OH)_2D_3$ five days after a primary immunization with HibCV resulted in a marked enhancement in antibody titres specific for both the polysaccharide and protein toxoid components of the vaccine. In addition, a significant elevation of the titres of IgA and IgG antibodies were also found in the vaginal secretions of the hormone treated animals. Similar results were obtained with lung washings as well.

EXAMPLE 5

Figure 7A:
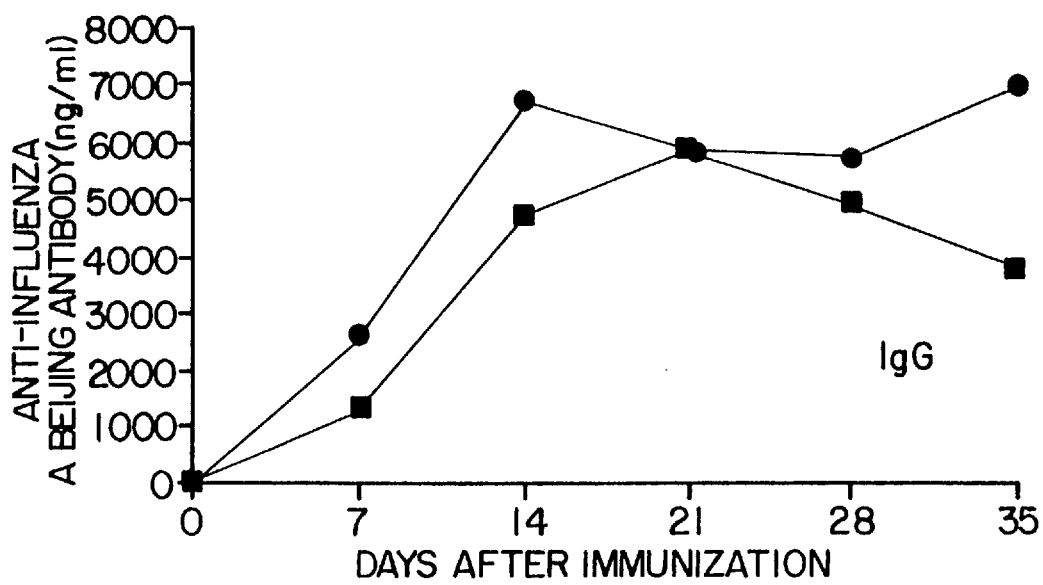
FIGS. 7A and 7B are graphs showing the effect of topically applied $1,25(OH)_2D_3$ on the serum antibody responses to immunization with virus vaccine (Influenza A/Beijing; 1.5 μg) in mice. Results from influenza virus-specific quantitative ELISA for IgG (FIG. 7A) and IgA (FIG. 7B) are shown for treated mice (data points ●), which received 1.0 μg of $1,25(OH)_2D_3$ on Day 5 following the primary immunization, and for untreated mice (data points ■), which received no $1,25(OH)_2D_3$.
Figure 7B:
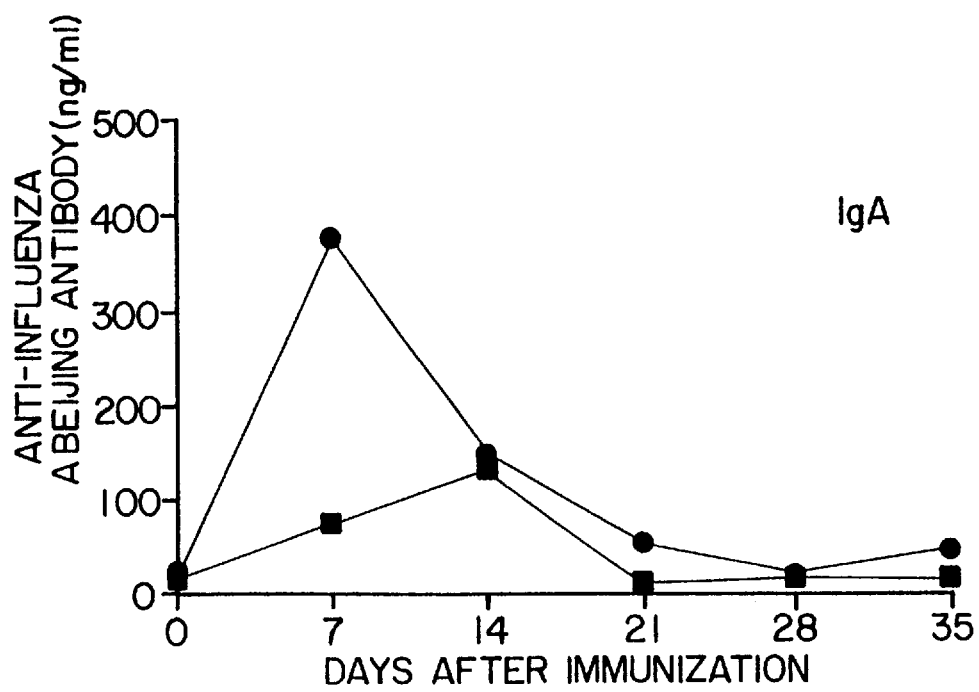
Figure 8A:
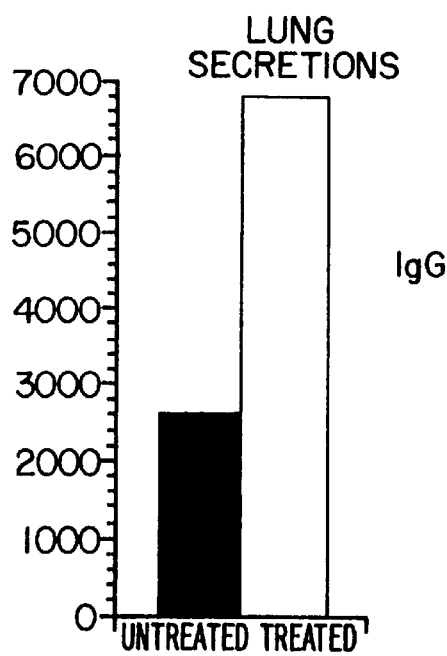
FIGS. 8A–8D are histograms showing the effect of topically applied $1,25(OH)_2D_3$ on mucosal immune responses in two different mucosal compartments to immunization with an influenza virus vaccine (Influenza A/Beijing), in mice. Results of Influenza A/Beijing virus-specific quantitative ELISA for IgG (FIGS. 8A, 8C) and IgA (FIGS. 8B, 8C) from vaginal lavages (FIGS. 8A, 8B) and lung lavages (FIGS. 8C, 8D) are shown for treated mice, which received 1.0 μg of $1,25(OH)_2D_3$ topically at the vaccination site on Day 5 following vaccination, and for untreated mice, which received no $1,25(OH)_2D_3$.
Figure 8C:
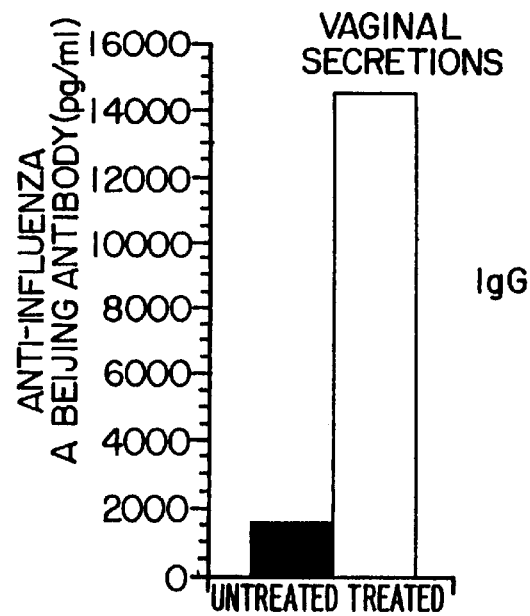
Figure 8B:
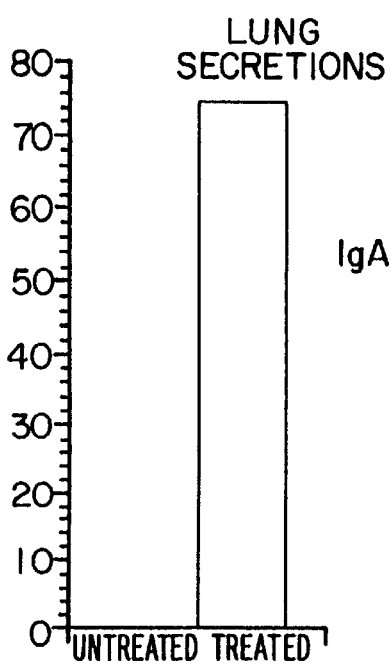
Figure 8D:
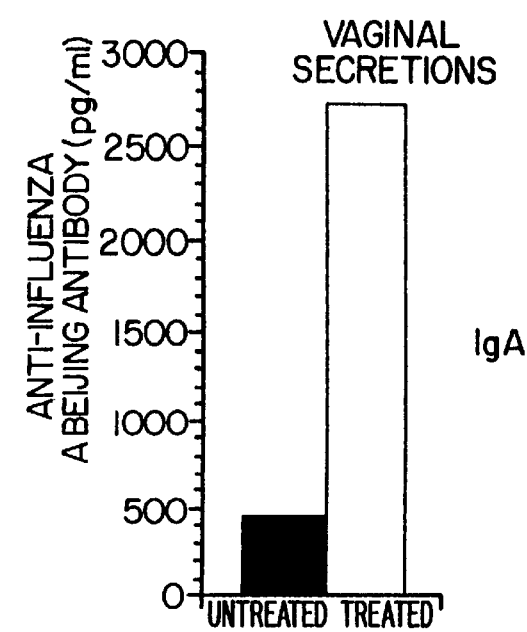

Administration of $1,25(OH)_2D_3$ Induces Immunoglobulin Production in Serum and Mucosal Tissue In a further demonstration, normal mature adult C3H/HeN strain animals were immunized subcutaneously with 1.5 µg of Influenza virus monovalent A/Beijing, obtained as a gift from Wyeth-Ayerst Labs, Marietta, Pa., with a standard aluminum hydroxide adjuvant. Five days after primary immunization, 1–2 µg of $1,25(OH)_2D_3$ in ethanol was applied epicutaneously to the immunization site of a "treated" group, and the remaining mice ("untreated mice") received only the ethanol carrier. At weekly intervals thereafter, serum samples were collected from individual animals and the levels of IgG and IgA antibodies specific for influenza virus antigens were analyzed by ELISA. The ELISA analyses for Influenza A/Beijing virus antibody employed a protocol identical to the standard protocol described above for Diphtheria toxoid antibody quantification except that influenza virus proteins were employed to coat the microtitre plates. The results are shown in FIGS. 7A and 7B. Twenty-one days following the primary immunization, some of the animals from the treated and untreated groups were sacrificed, and lung lavages were obtained by injecting 0.7 ml of PBS into the trachea, flushing in and out 5–7 times, and finally drawing the lavage fluid into the syringe. Samples were clarified by centrifugation prior to quantitative analysis for IgG and IgA antibody amounts by ELISA. The remaining animals were sacrificed at 14 days following a secondary immunization (without further treatment with the lymphoid organ modifier) and lung lavage samples were collected and analyzed in a similar manner. The results, shown in FIGS. 8A–8D, demonstrate a mucosal response in two different mucosal compartments (urogenital tract and lungs).

EXAMPLE 6

Figure 9A:
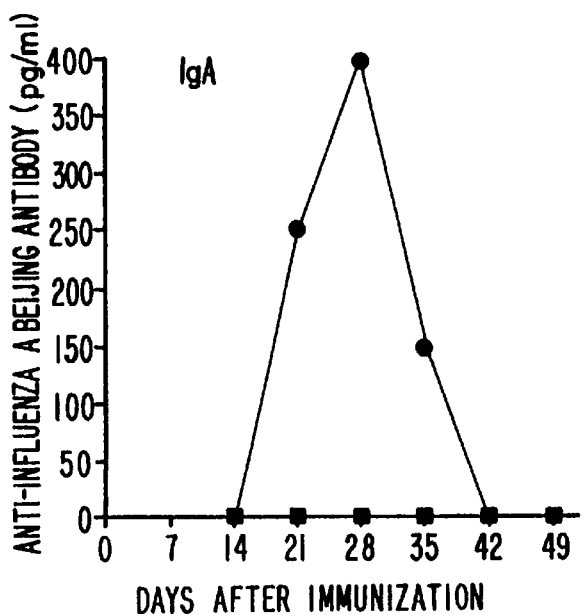
FIGS. 9A and 9B show that IgA production is induced in mucosal tissue with administration of $1,25(OH)_2D_3$ incorporated in the vaccine. The IgA responses are shown for mice without $1,25(OH)_2D_3$ treatment (●) and for mice with $1,25(OH)_2D_3$ treatment (■).
Figure 9B:
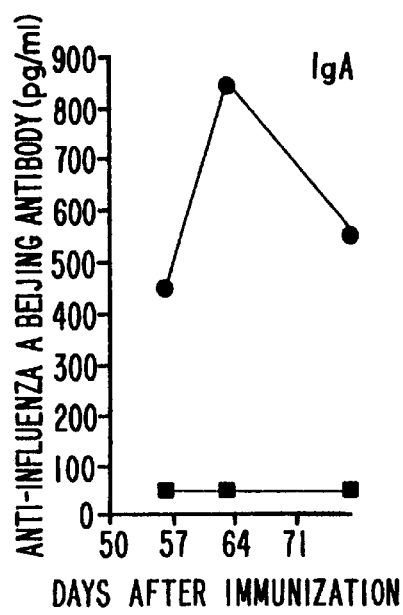
Figure 9C:
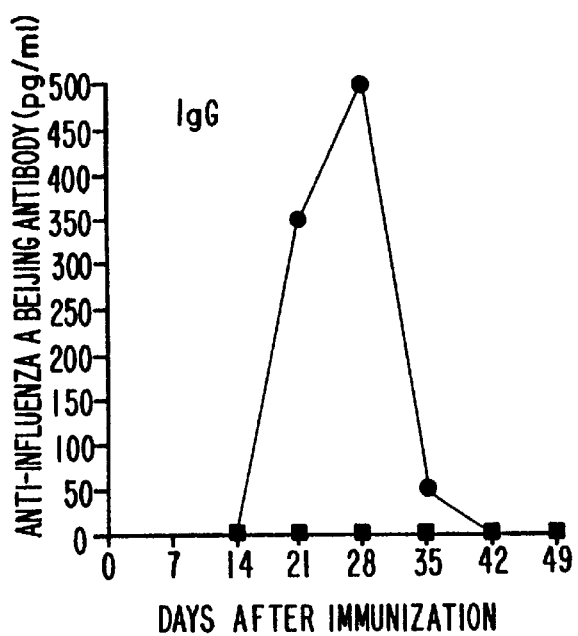
FIGS. 9C and 9D show that IgG production is induced in mucosal tissue with administration of $1,25(OH)_2D_3$ incorporated in the vaccine. The IgG responses are shown for mice without $1,25(OH)_2D_3$ treatment (■) and for mice with $1,25(OH)_2D_3$ treatment (●).
Figure 9D:
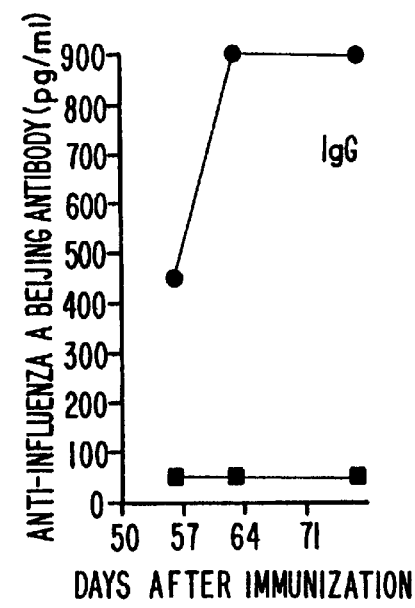

Administration of $1,25(OH)_2D_3$ Induces Immunoglobulin Production in Mucosal Tissue Ten mature adult CBA mice were immunized with 0.1 µg inactivated Influenza-A Beijing strain in 25 µl alum (273 µg/ml) in the hind footpad, wherein 0.1 µg of $1,25(OH)_2D_3$ was incorporated into the vaccine mixture. Individual samples were collected at weekly intervals during the primary response. All animals were boosted with 0.1 µg of the inactivated Influenza-A virus in 25 µl alum in the hind footpad. Recall responses were stimulated without any additional treatment with $1,25(OH)_2D_3$. The mean quantities of antibody detected in mucosal secretions during both primary and secondary responses are shown in FIGS. 9A and 9B for IgA, and FIGS. 9C and 9D for IgG, which demonstrate the induction of immunoglobulin production in mucosal tissue.

EXAMPLE 7

Figure 10A:
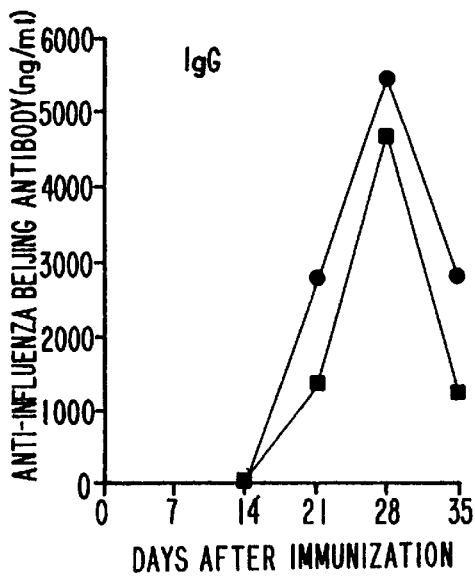
FIGS. 10A and 10B show that IgG production is induced in serum with topical administration of $1,25(OH)_2D_3$ five days after administration of vaccine. The IgG responses are shown for mice without $1,25(OH)_2D_3$ treatment (■) and for mice with $1,25(OH)_2D_3$ treatment (●).
Figure 10B:
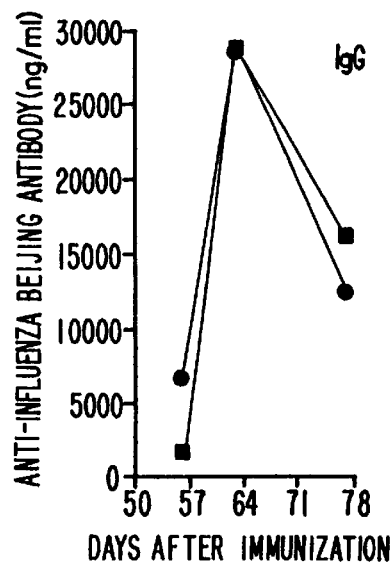
Figure 10C:
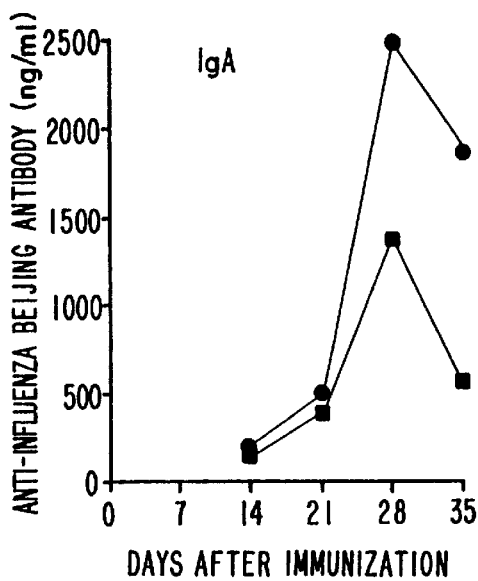
FIGS. 10C and 10D show that IgA production is induced in serum with topical administration of $1,25(OH)_2D_3$ five days after administration of vaccine. The IgA responses are shown for mice without $1,25(OH)_2D_3$ treatment (■) and for mice with $1,25(OH)_2D_3$ treatment (●).
Figure 10D:
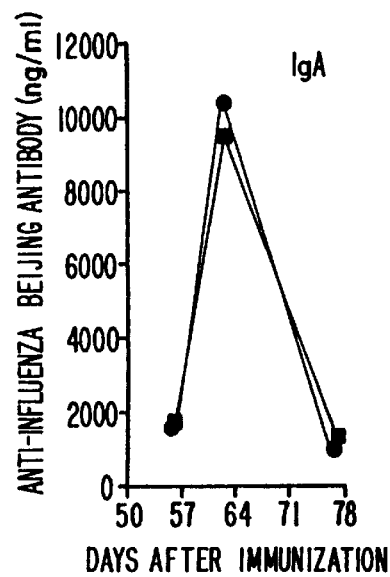

Topical Administration of $1,25(OH)_2D_3$ Induces Immunoglobulin Production in Mucosal Tissue Ten mature adult C3H mice were immunized with 0.1 µg inactivated Influenza-A Beijing strain in 25 µl alum (273 µg/ml) in the hind footpad. Five days later, half of the immunized mice were administered 2 µg of $1,25(OH)_2D_3$ topically at the same site of immunization. Individual serum and vaginal lavage samples were collected at weekly intervals during the primary response. All animals were boosted with 0.1 µg of the inactivated Influenza-A virus in 25 µl alum in the hind footpad. Recall responses were stimulated without any additional treatment with $1,25(OH)_2D_3$. The mean quantities of antibody detected in both serum and mucosal secretions during both primary and secondary responses are shown in FIGS. 10A–10D and 11A–11D. FIGS. 10A and 10B show serum IgG production, and FIGS. 10C and 10D show serum IgA production. FIGS. 11A and 11B show mucosal IgA production, and FIGS. 11C and 11D show IgG production.

EXAMPLE 8

Figure 12:
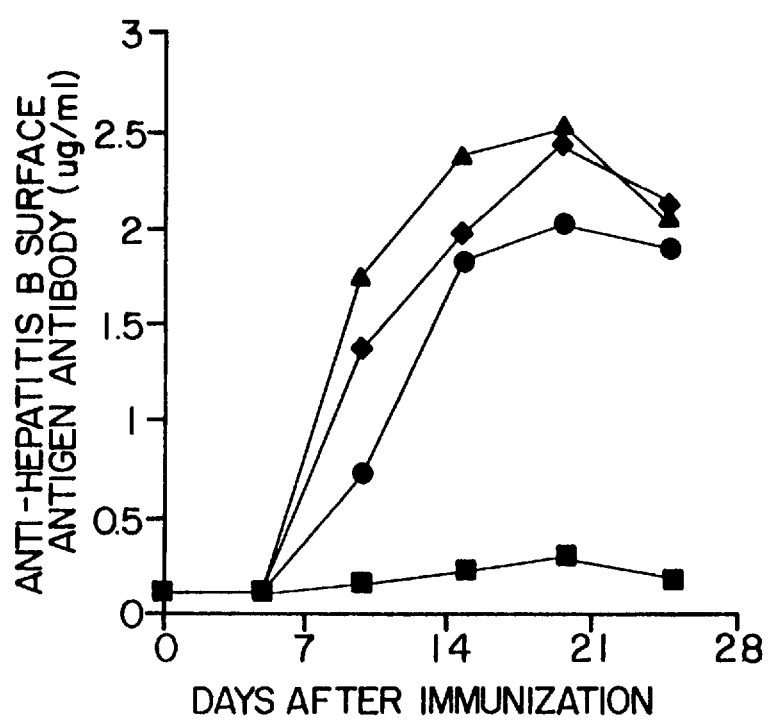
FIG. 12 shows that the antibody response in aged mice, following vaccination with rHBSAg, is enhanced by treatment with DHEA or DHEA-S. The antibody responses are shown for aged mice without treatment (■), aged mice with topical DHEA treatment (●), aged mice with DHEA incorporated in the vaccine (▲), and aged mice with DHEA-S incorporated in the vaccine (♦).
Figure 14A:
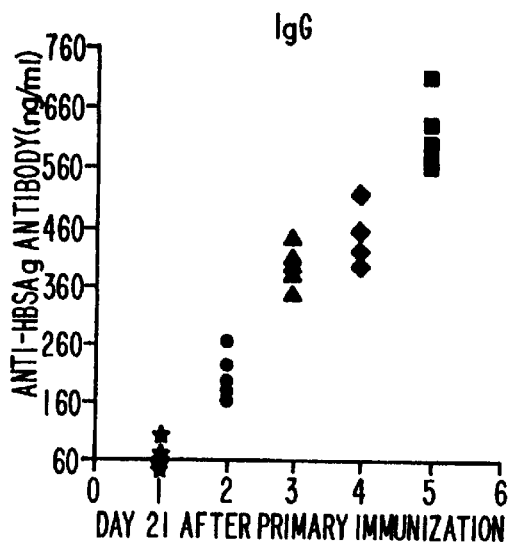
FIGS. 14A and 14B show that serum (systemic) antibody response in mature mice following vaccination with rHBSAg is synergistically enhanced by treatment with DHEA and $1,25(OH)_2D_3$. Antibody responses at Day 21 are shown for non-immunized mice (★), mice without treatment (●), mice treated with 2 μg DHEA in vaccine (♦), mice treated with 0.1 μg $1,25(OH)_2D_3$ in vaccine (▲), and mice treated with 2 μg DHEA and 0.1 μg $1,25(OH)_2D_3$ in vaccine (■).
Figure 14B:
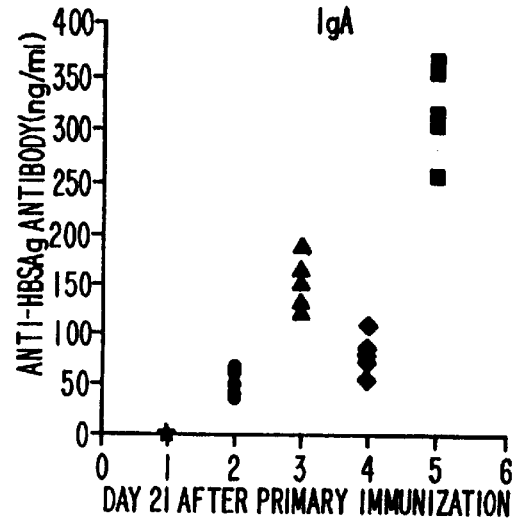
Figure 14C:
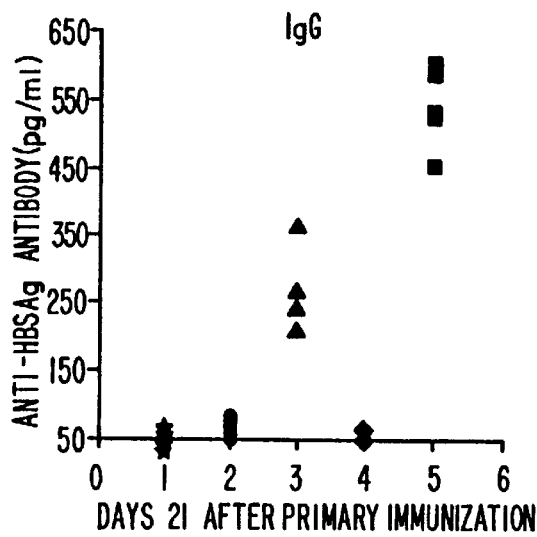
FIGS. 14C and 14D show that mucosal antibody response in mature mice following vaccination with rHBSAg is synergistically enhanced by treatment with DHEA and $1,25(OH)_2D_3$. Antibody responses at Day 21 are shown for non-immunized mice (★), mice without treatment (●), mice treated with 2 μg DHEA in vaccine (♦), mice treated with 0.1 μg $1,25(OH)_2D_3$ in vaccine (▲), and mice treated with 2 μg DHEA and 0.1 μg $1,25(OH)_2D_3$ in vaccine (■).
Figure 14D:
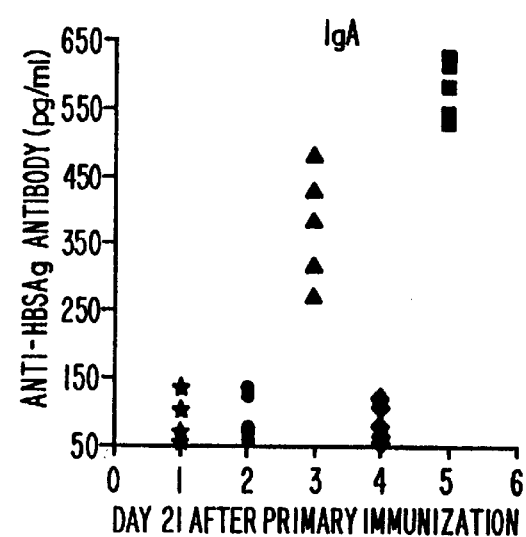
Figure 15A:
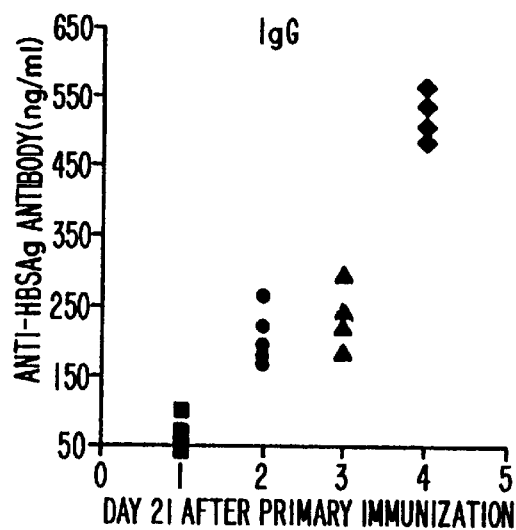
FIGS. 15A and 15B show that serum (systemic) antibody response in mature mice following vaccination with rHBSAg is synergistically enhanced by treatment with DHEA and all trans-retinoic acid. Antibody responses at Day 21 are shown for non-immunized mice (■), mice without treatment (●), mice treated with 5.0 μg all trans-retinoic acid in vaccine (▲), and mice treated with 2 μg DHEA and 5.0 μg all trans-retinoic acid in vaccine (♦).
Figure 15B:
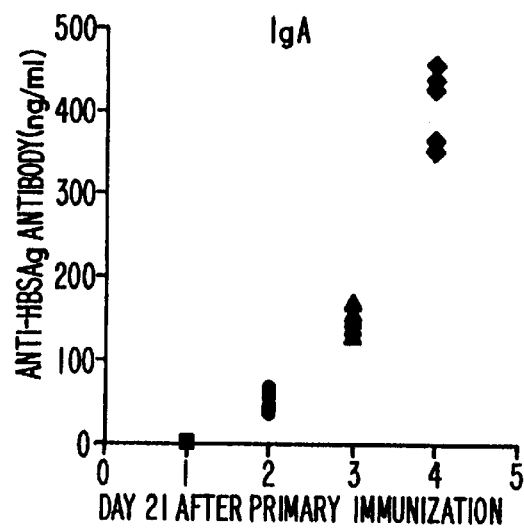
Figure 15C:
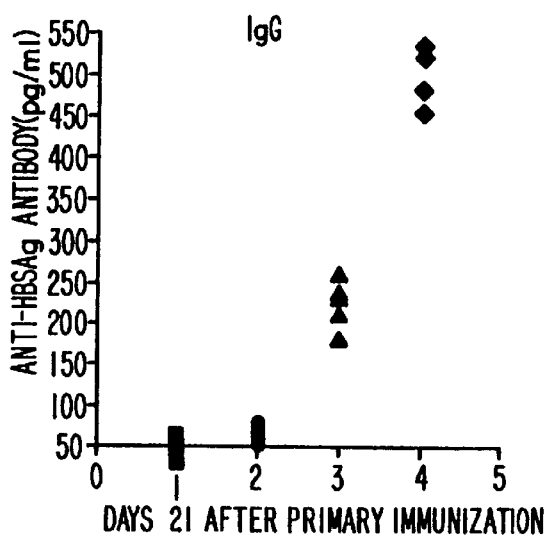
FIGS. 15C and 15D show that mucosal antibody response in mature mice following vaccination with rHBSAg is synergistically enhanced by treatment with DHEA and all transretinoic acid. Antibody responses at Day 21 are shown for non-immunized mice (■), mice without treatment (●), mice treated with 5.0 μg all trans-retinoic acid in vaccine (▲), and mice treated with 2 μg DHEA and 5.0 μg all trans-retinoic acid in vaccine (♦).
Figure 15D:
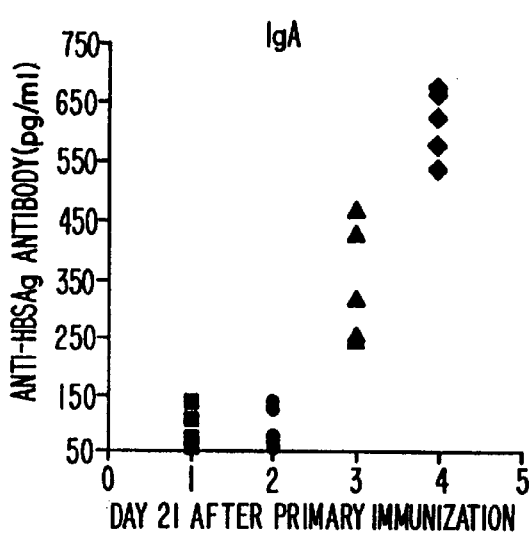

Administration of DHEA or DHEA-S Topically or as a Component of the Vaccine Enhanced Antibody Production Groups of sex- and age-matched mice [(C3H×C57 BL/6) F1], greater than 24 months of age, were immunized subcutaneously with rHBSAg (1.0 µg in 25 µl alum (273 µg/ml)). Animals were given a topical administration of 10 µg DHEA three hours prior to vaccination. Alternatively, 10 µg DHEA or DHEA-S was incorporated into the vaccine/alum mixture prior to immunization. Untreated aged mice were administered the ethanol vehicle without DHEA. Serum samples were collected from individual mice at multiple times and were evaluated by quantitative ELISA as described above, to determine the amount of HbSAg-specific antibody. The mean antibody response is shown in FIG. 12. The results show that the serum antibody response was enhanced in aged mice when the mice were treated prior to vaccination with topical DHEA (●) or were treated with DHEA (▲) or DHEA-S (♦) incorporated in the vaccine.

Similar results are obtained when DHEA congeners of formula I as set forth in Table A are used in place of DHEA or DHEA-S.

TABLE A

DHEA Congeners Useful for Vaccine Enhanced Antibody Production

| $R^1$ | $R^2$ | $R^3$ | X |
|---|---|---|---|
| O | O | H | H |
| OOCC$_2$H$_5$ | O | H | Br |
| OCH$_5$ | O | H | H |
| SH | O | H | H |
| SOC(CH$_2$)$_5$CH$_3$ | O | H | H |
| SCH$_3$ | O | H | H |
| O | O | OH | H |
| OH | O | O | Br |
| OH | O | OOC(CH$_2$)$_2$C$_6$H$_5$ | H |
| OH | O | OOCC$_2$H$_5$ | H |
| OH | O | OH | H |
| SH | O | SH | H |
| SCH$_3$ | O | SH | H |
| OH | OH | H | H |
| O | OH | H | Br |
| OH | OOCC$_2$H$_5$ | H | H |
| OH | OC$_2$H$_4$ | H | H |
| SH | OH | H | H |
| SCH$_3$ | OH | H | H |
| O | OH | O | H |
| OH | OH | O | Br |
| cypionate | OOCH$_3$ | O | H |
| OH | OH | OH | H |
| SH | OH | SH | H |
| SH | OH | SCH$_3$ | H |
| OH | SH | H | H |
| OH | SH | H | Br |
| OOC(CH$_2$)$_2$CO$_2$H | SH | H | H |
| SH | SH | H | H |
| SH | SC$_2$H$_4$ | H | H |
| O | SH | OH | H |
| OC$_2$H$_5$ | SH | OH | H |
| SOCCH$_3$ | SH | SH | H |
| SH | SCH$_3$ | SH | H |
| glucuronate | O | O | H |
| OSO$_2$OH | O | OH | H |
| OH | OSO$_2$OH | OH | H |
| OSO$_2$OCC$_4$H$_9$ | O | OH | H |
| OP(O)(OH)OCCH$_3$ | O | O | H |

EXAMPLE 9

Topical Administration of DHEA Enhances Serum Antibody Production in Elderly Mice Upon Vaccination This example demonstrates that topical administration of DHEA prior to vaccination against several different antigens enhances serum antibody production in elderly mice.

Aged mice [C3H/HeN], approximately 22–27 months of age, were given a topical application of 10 μg DHEA three hours prior to vaccination with Diphtheria toxoid (Dt, 1.0 μg), Tetanus toxoid (Tt, 1.0 μg), or a Hemophilus Influenza-Type b conjugate vaccine coupled to Dt (500 ng of Hib polysaccharide chemically coupled to 1.25 μg Dt) in standard alum adjuvant. Untreated aged mice and untreated mature adult mice [C3H/HeN], 17–24 weeks of age, were administered the ethanol vehicle without DHEA. Serum samples were collected from individual mice at multiple times during the primary response. Individual serum samples were evaluated by quantitative ELISA as described above, using purified Dt (diluted in 0.05M Tris-HCl (pH 9.6) at a concentration of 2.0 μg/ml), purified Tt (diluted in 0.05M Tris-HCl (pH 9.6) at a concentration of 2 μg/ml), or Hib-meningococcal protein conjugate (diluted in 0.05M Tris-HCl (pH 9.6) at a concentration of 200 ng/ml polysaccharide). The mean primary antibody response at Day 28 is shown in Table 1. The results show that the serum antibody responses to these antigens were enhanced in aged mice with topical administration of DHEA prior to vaccination. Similar results were obtained when DHEA is incorporated in the vaccine.

TABLE 1

Serum Antibody Production

Primary Antibody Response (μg/ml)

| Immunogen | Mature Adult | Aged | DHEA-treated Aged |
|---|---|---|---|
| Diphtheria Toxoid (1.0 μg) | 1.65 | 0.43 | 5.75 |
| Tetanus Toxoid (1.0 μg) | 6.8 | 2.3 | 4.6 |
| Hemophilus Influenza Type b Conjugate Vaccine: | | | |
| Hib Polysaccharide (500 ng) | 13.3 | 6.4 | 16.2 |
| Diphtheria Toxoid (1.25 μg) | 5.8 | 3.5 | 7.8 |

EXAMPLE 10

Administration of DHEA-S in Vaccine Enhances Serum Antibody Production in Elderly Mice Example 9 demonstrates that topical administration of DHEA prior to immunization enhanced the production of serum antibodies in elderly mice. This Example demonstrates that administration of DHEA-S in the antigen vehicle also enhances serum antibody production in elderly mice.

Aged mice [C3H/HeN], 22–27 months of age, were vaccinated with inactivated Influenza-A Beijing strain (0.1 μg) in a standard alum adjuvant (25 μl; 273 μg alum/ml) which also contained 10 μg DHEA-S. Untreated aged mice and untreated mature adult mice [C3H/HeN], 17–24 weeks of age, were administered the vaccine without DHEA-S. Serum samples were collected from individual mice at multiple times during the primary response. Individual serum samples were evaluated by quantitative ELISA as described above, using purified inactivated Influenza A (diluted in 0.05M Tris-HCl (pH 9.6) at a concentration of 0.1 μg/ml). The mean primary antibody response at Day 28 is shown in Table 2. The results show that the serum antibody response to this antigen was enhanced in aged mice with incorporation of DHEA-S in the vaccine.

Similar results are obtained for the DHEA congeners of Table 1 when substituted for DHEA.

TABLE 2

Serum Antibody Production

Primary Antibody Response (mg/ml)

| Immunogen | Mature Adult | Aged | DHEA-treated Aged |
|---|---|---|---|
| Inactivated Influenza A Virus (0.1 μg) | 4.7 | 0.16 | 4.3 |

EXAMPLE 11

Administration of 1,25(OH)$_2$D$_3$ Enhances Antibody Response to Vaccinations with Various Antigens Sex- and age-matched mice [CF-1] were immunized subcutaneously with the following antigens in alum (273 µg/ml):

Chlamydia trachomatus peptide (5 µg)
Hemophilus Influenza untypeable (1.0 µg)
Hemophilus Influenza Type b conjugate vaccine coupled to Dt (500 ng of Hib polysaccharide chemically coupled to 1.25 µg Dt)
Respiratory syncytial virus peptide (1 µg)
Hepatitis B Surface Antigen (1 µg)
HIV gp 120 (0.5 µg)
Neisseria gonorrhoeae pilin protein (1 µg)
Diphtheria toxoid (1 µg)

One group of mice was administered 2 µg 1,25(OH)$_2$D$_3$ epicutaneously at the same site on Day 0. Untreated mice were administered the ethanol vehicle without 1,25(OH)$_2$D$_3$. Serum samples and mucosal samples (vaginal lavage samples (75 µl of physiological saline)) were collected from individual mice at multiple times during the primary response. Individual serum and mucosal samples were evaluated by quantitative ELISA as described above, using the appropriate antigens. The mean primary antibody responses at Day 28 are shown in Table 3 for the serum (systemic or humoral) antibodies and in Table 4 for the mucosal antibodies. The results show that the serum and mucosal antibody responses were enhanced in mice with topical administration of 1,25(OH)$_2$D$_3$. Mucosal antibodies (both IgG and IgA) were also detected in other mucosal secretions including lacrimal, rectal, oral and lung. Similar results were obtained when all trans-retinoic acid is used in place of 1,25(OH)$_2$D$_3$.

TABLE 3

Secretory Antibody Production

| | Systemic Ig (ng/ml) | | | |
|---|---|---|---|---|
| | Vaccine Only | | Vaccine With Topical 1.25(OH)$_2$D$_3$ | |
| | IgG | IgA | IgG | IgA |
| Chlamydia trachomatus peptide (5 µg) | <0.02 | 43 | 55 | 85 |
| Hemophilus influenza untypeable | 3235 | 69 | 4712 | 93.2 |
| Hemophilus Influenza type b-CV: | | | | |
| Hib polysaccharide (500 ng) | 25 | 12.5 | 125 | 76.1 |
| Diphtheria toxoid (1.25 µg) | 853 | 11.6 | 1285 | 20.3 |
| Respiratory Syncytial virus peptide (1 µg) | 2746 | 225 | 8440 | 754 |
| Hepatitis B surface antigen (1 µg) | 254 | 58 | 902 | 149 |
| HIV gp120 (.5 µg) | 1356 | 854 | 2459 | 1408 |
| Neisseria gonorrhoeae pilin protein (1 µg) | 844 | 16.3 | 1841 | 29.1 |
| Diphtheria toxoid (1 µg) | 1233 | 23 | 1640 | 137 |

TABLE 4

Secretory Antibody Production

| | Mucosal Ig (ng/ml) | | | |
|---|---|---|---|---|
| | Vaccine Only | | Vaccine With Topical 1.25(OH)$_2$D$_3$ | |
| | IgG | IgA | IgG | IgA |
| Chlamydia trachomatus peptide (5 µg) | <20 | 397 | 759 | 2234 |
| Hemophilus Influenza untypeable | 719 | 1384 | 2081 | 1865 |
| Hemophilus Influenza type b-CV: | | | | |
| Hib polysaccharide (500 ng) | 180 | 440 | 280 | 1720 |
| Diphtheria toxoid (1.25 µg) | 310 | 400 | 590 | 1400 |
| Respiratory Syncytial virus peptide (1 µg) | <20 | <20 | 1544 | 1264 |
| Hepatitis B surface antigen (1 µg) | <20 | <20 | 450 | 250 |
| HIV gp120 (.5 µg) | 35 | 45 | 1428 | 755 |
| Neisseria gonorrhoeae pilin protein (1 µg) | 6341 | 1063 | 10235 | 5486 |
| Diphtheria toxoid (1 µg) | <20 | 60 | 1.8 | 1125 |

The above example was repeated, using 0.1 µg 1,25(OH)$_2$D$_3$ in the vaccine (in a total volume of 25 µl with alum (250 µg/ml)) instead of topical administration of the 1,25(OH)$_2$D$_3$. Identical results were obtained as set forth in Tables 3 and 4.

EXAMPLE 12

Analysis of Influenza-Specific Antibodies and Antibody Secreting Cells

Groups of sex- and age-matched mice [C3H/HeN], 17–24 weeks of age, were immunized with 0.1 µg monovalent, inactivated Influenza-A virus (Beijing strain) in the hind footpad in a 25 µl volume of alum (273 µg/ml). Half of the immunized mice were treated with 1 µg 1,25(OH)$_2$D$_3$ by topical application at the site of immunization, five days after immunization. After 21 days following immunization, spleens and lungs of two individual mice were dissociated in a balanced salt solution. Lung tissue was further dissociated in collagenase using a modification of the method of Davies and Parsot ((1981), *Gut* 22:481–488). Detection of antibody-secreting cells was performed on antigen-coated, nitrocellulose-backed 96-well microtitre plates, with biotinylated goat anti-mouse heavy chain-specific antibodies, avidin-alkaline phosphatase, and BCIP and NBT substrates (Sedgwick and Holt (1986). *J. Immunol. Meth.* 87:37–44). The mean (±SEM) number of spot-forming cells/10$^6$ cells was determined, and the results are shown in Table 5.

TABLE 5

Analysis of Influenza-Specific Antibody-Secreting Cells by Elispot

| | IgG | | IgA | |
| --- | --- | --- | --- | --- |
| Tissue Assayed | Vaccine Only | Vaccine w/Topical 1,25(OH)$_2$D$_3$ | Vaccine Only | Vaccine w/Topical 1,25(OH)$_2$D$_3$ |
| Spleen | 4800 (410) | 6700 (730) | 670 (56) | 4400 (460) |
| Lung | 20 (3) | 650 (55) | 20 (2) | 320 (37) |

In addition, lacrimal, oral, vaginal and colorectal mucosa were swabbed with a prewetted cotton sponge (1–2 mm diameter), 28 days after immunization. The swab was then rinsed into a small volume (50 μl) of buffer which released the absorbed immunoglobulins. The samples were frozen at −20° C. until assessment. Immunoglobulins were detected using a micro dot-blot analysis with goat anti-mouse heavy chain-specific antibodies. The reactivity of each sample for nitrocellulose-bound antigen (Influenza) was equated with the detection of murine IgG and IgA standards. Negative reactions gave undetectable binding (a predicted value of <10 pg/ml). Positive detection ranged from + to +++, where + had an approximate value of 50–100 pg/ml, ++ had an approximate value of 200 pg/ml, and +++ had an approximate value of 500–1000 pg/ml. The results of this analysis are shown in Table 6, which demonstrates production of secretory immunoglobulin in all mucosal samples tested.

TABLE 6

Influenza-Specific Secretory Immunoglobulin

| | IgG | | IgA | |
| --- | --- | --- | --- | --- |
| Mucosal Epithelium | Vaccine Only | Vaccine with D$_3$ | Vaccine Only | Vaccine with D$_3$ |
| Lacrimal | − | +++ | − | +++ |
| Oral | − | +++ | − | +++ |
| Vaginal | − | +++ | − | +++ |
| Colorectal | − | + | − | + |

EXAMPLE 13

Comparative Effect of 1,25(OH)$_2$D$_3$ and All Trans-Retinoic Acid on Immunoglobulin Production Groups of sex- and age-matched mice [CF-1], 17–24 weeks of age, were immunized with 1.0 μg HBSAg in 25 μl alum. The mice in each group were immunized with either vaccine alone, vaccine with 0.1 μg 1,25(OH)$_2$D$_3$, or vaccine with 5 μl all trans-retinoic acid. The agents were incorporated directly into the vaccine mixture. Individual serum (systemic) samples and mucosal samples (vaginal lavage samples (75 μl of physiological saline)) were collected at weekly intervals during the primary response. The mean quantities of antibodies (IgG and IgA) detected in the serum and mucosal secretions 28 days after a single immunization are shown in Table 7. The results show that both 1,25(OH)$_2$D$_3$ and all trans-retinoic acid enhance both the serum and mucosal antibody response.

TABLE 7

Antibody Production with 1,25(OH)$_2$D$_3$ or All Trans-Retinoic Acid

| Composition of Vaccine | Systemic Ig (ng/ml) | | Mucosal Ig (ng/ml) | |
| --- | --- | --- | --- | --- |
| | IgG | IgA | IgG | IgA |
| Vaccine only | 225 | 160 | 35 | <20 |
| Vaccine w/ 0.1 μg 1,25(OH)$_2$D$_3$ | 457 | 494 | 352 | 341 |
| Vaccine w/ 5 μg All Trans-Retinoic Acid | 295 | 531 | 437 | 311 |

EXAMPLE 14

Administration of DHEA and 1,25(OH)$_2$D$_3$ in Vaccine Enhances Serum and Mucosal Antibody Response Groups of five mature adult C3H mice were immunized with 0.1 μg inactivated Influenza-A Beijing strain in 25 μl of alum (273 μg/ml) in the hind footpad. The mice in each group were immunized with either vaccine alone, vaccine plus 2 μg DHEA, vaccine plus 0.1 μg of 1,25(OH)$_2$D$_3$, or vaccine with both 2 μg DHEA and 0.1 μg 1,25(OH)$_2$D$_3$. The agents were incorporated directly into the vaccine mixture. Individual serum (systemic) samples and mucosal samples (vaginal lavages (75 μl of physiological saline)) were collected at weekly intervals during the primary response. FIGS. 13A–13D show the mean quantities of antibody detected in serum (A and B) and mucosal secretions (C and D) 28 days after a single immunization. The results show that co-administration of DHEA and 1,25(OH)$_2$D$_3$ in the vaccine synergistically enhances both the serum and mucosal antibody response.

EXAMPLE 15

Administration of DHEA and 1,25(OH)$_2$D$_3$ in Vaccine Enhances Serum and Mucosal Antibody Response Groups of five mature adult CF1 mice were immunized with 1.0 μg rHBSAg in 25 μl of alum (273 μg/ml) in the hind footpad. The mice in each group were immunized with either vaccine alone, vaccine plus 2 μg DHEA, vaccine plus 0.1 μg of 1,25(OH)$_2$D$_3$, or vaccine with both 2 μg DHEA and 0.1 μg 1,25(OH)$_2$D$_3$. The agents were incorporated directly into the vaccine mixture. Individual serum (systemic) samples and mucosal samples (vaginal lavages (75 μl of physiological saline)) were collected at weekly intervals during the primary response. FIGS. 14A–14D show the mean quantities of antibody detected in serum (A and B) and mucosal secretions (C and D) 21 days after a single immunization. The results show that coadministration of DHEA and 1,25(OH)$_2$D$_3$ in the vaccine synergistically enhances both the serum and mucosal antibody response.

Similar results are obtained for the DHEA congeners of Table 1 when substituted for DHEA.

EXAMPLE 16

Administration of DHEA and All Trans-Retinoic Acid in Vaccine Enhances Serum and Mucosal Antibody Response Groups of five mature adult CF1 mice were immunized with 1.0 μg rHBSAg in 25 μl of alum (273 μg/ml) in the hind footpad. The mice in each group were immunized with either vaccine alone, vaccine plus 5.0 μg of all trans-retinoic acid, or vaccine with both 2 μg DHEA and 5.0 μg all trans-retinoic acid. The agents were incorporated directly into the vaccine mixture. Individual serum (systemic) samples and mucosal samples(vaginal lavages (75 μl of physiological saline)) were collected at weekly intervals during the primary response. FIGS. 15A–15D show the mean quantities of antibody detected in serum (A and B) and mucosal secretions (C and D) 21 days after a single immunization. The results show that co-administration of DHEA and all trans-retinoic acid in the vaccine synergistically enhances both the serum and mucosal antibody response.

EXAMPLE 17

Administration of $1,25(OH)_2$-16-ene Vitamin $D_3$ in Vaccine Enhances Serum and Mucosal Antibody Response Groups of mature adult CF1 mice were immunized with 1.0 μg rHBSAg in 25 μl of alum (273 μg/ml) in the hind footpad. The mice in each group were immunized with either vaccine alone, vaccine plus 0.1 μg $1,25(OH)_2D_3$, or 0.1 μg $1,25(OH)_2$-16-ene $D_3$. The agents were incorporated directly into the vaccine mixture. Antibody production was followed over 30 days in individual serum samples, fecal samples and mucosal samples (vaginal lavages (75 μl of physiological saline)). Identical results were obtained with both $1,25(OH)_2D_3$ and $1,25(OH)_2$-16-ene $D_3$. These results were identical to those reported in the previous examples, i.e., an increase in both serum and mucosal IgG and IgA antibody levels when compared to the vaccine alone. In addition, increased IgA antibodies were seen in fecal samples for the vaccines containing $1,25(OH)_2D_3$ and $1,25(OH)_2$-16-ene $D_3$, when compared to the vaccine alone.

The immunized mice were then challenged with 2.0 μg rHBSAg intranasally, and antibody production followed for 10 days. The antibody titres were measured in lung lavages (75 μl physiological saline) and in feces. The titre of anti-rHBSAg antibodies (IgG and IgA) was elevated for both the vaccines containing $1,25(OH)_2D_3$ or $1,25(OH)_2$-16-ene $D_3$ compared to vaccine alone. The titre of IgA in feces was also elevated but not as great as in the lung lavages.

EXAMPLE 18

Topical Administration of Calcipotriene Enhances Serum and Mucosal Antibody Response Groups of mature adult mice were immunized with 0.1 μg rHBSAg in 25 μl alum (273 μg/ml) in the hind footpad. One-third of the mice were treated with 0.5 μg $1,25(OH)_2D_3$ by topical application at the site of immunization, 5 days after immunization. One-third of the mice were similarly treated with 0.5 μg calcipotriene. Antibody production was followed over 30 days in individual serum samples, fecal samples and mucosal samples (vaginal lavages (75 μl of physiological saline)). Identical results were obtained with $1,25(OH)_2D_3$ as previously noted, i.e., increased production of serum and mucosal IgG and IgA antibodies in serum and mucosal secretions when compared to vaccine alone. In addition, increased production of IgA was seen in fecal samples when compared to vaccine alone.

Similar results as seen with $1,25(OH)_2D_3$ were seen with calcipotriene except the serum IgG levels were not elevated as much as with $1,25(OH)_2D_3$.

EXAMPLE 19

Figure 16A:
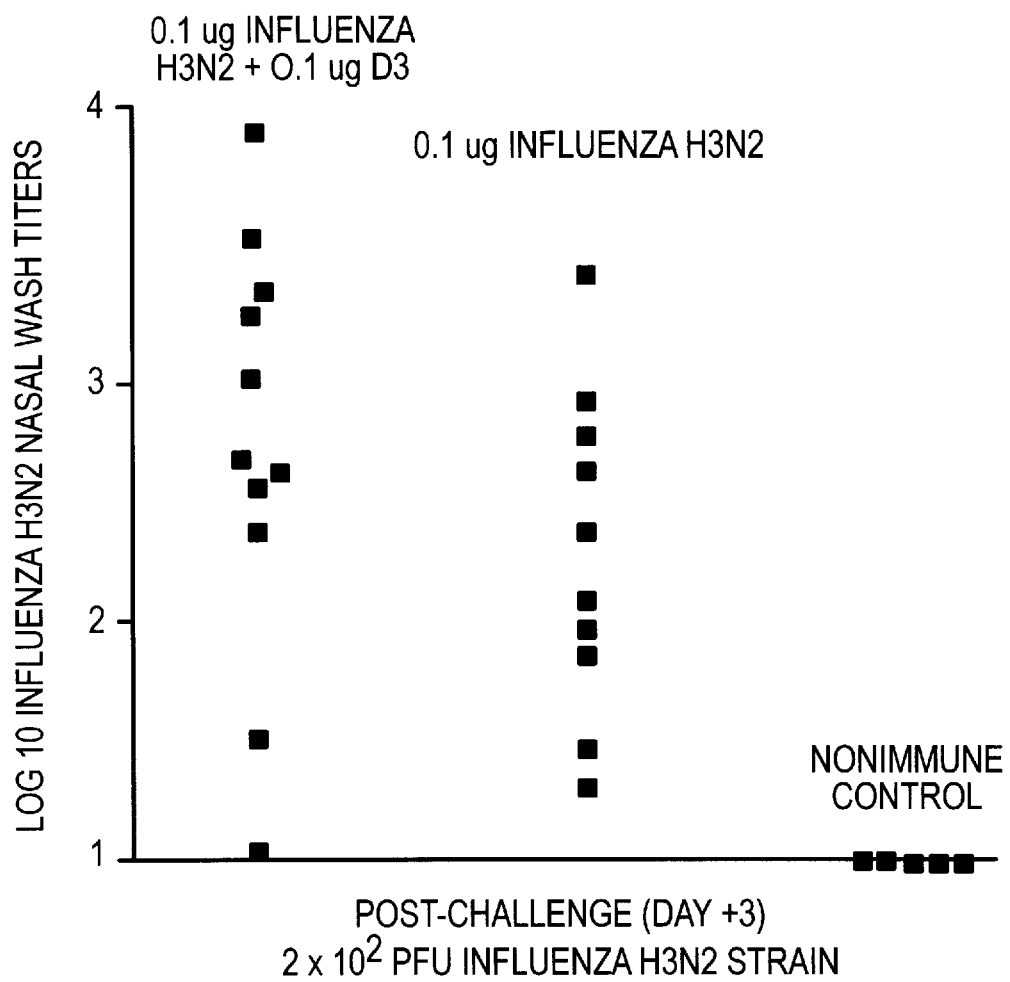
FIG. 16A shows the titre of antigen-specific antibody in nasal wash fluid.
Figure 16B:
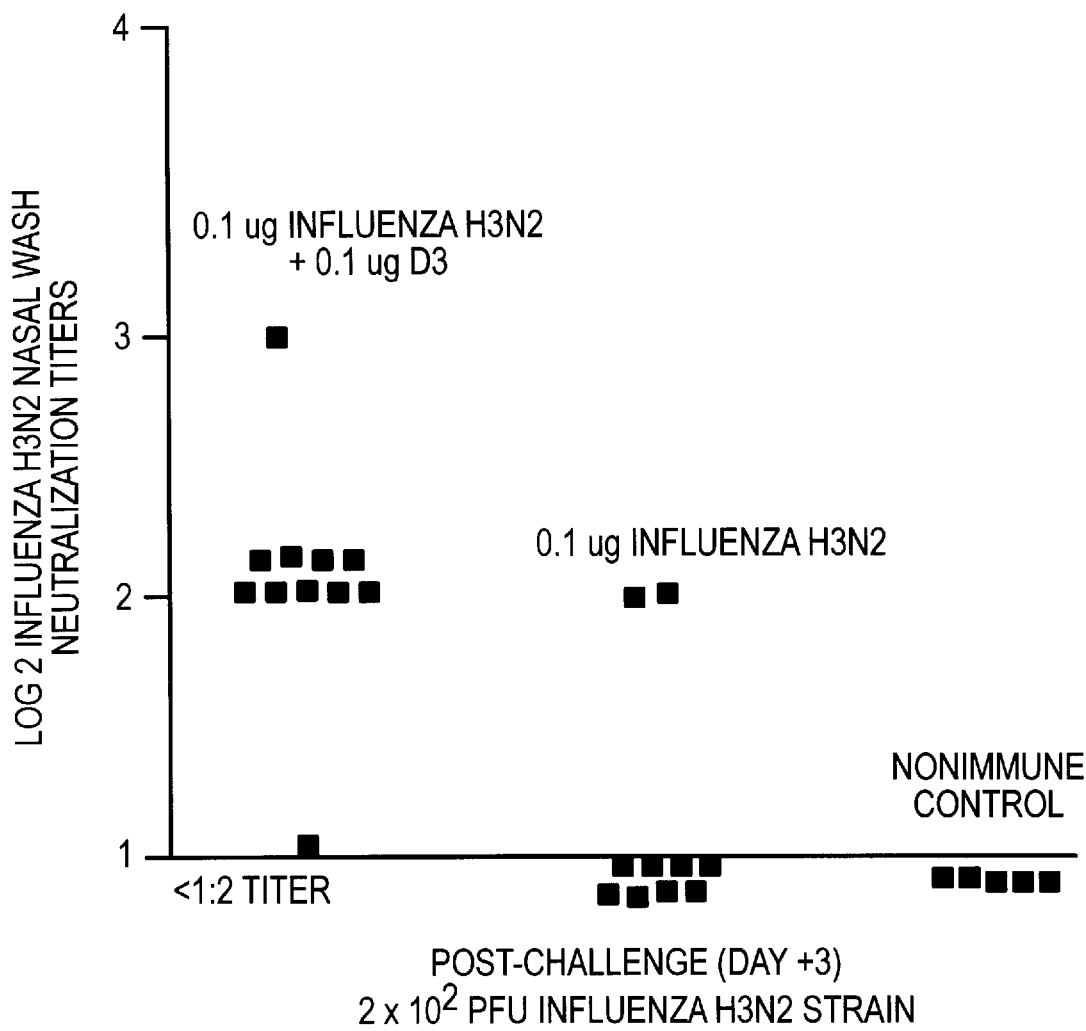
FIG. 16B shows the specific neutralizing activity of nasal wash fluid as measured by hemagglutination inhibition.
Figure 16C:
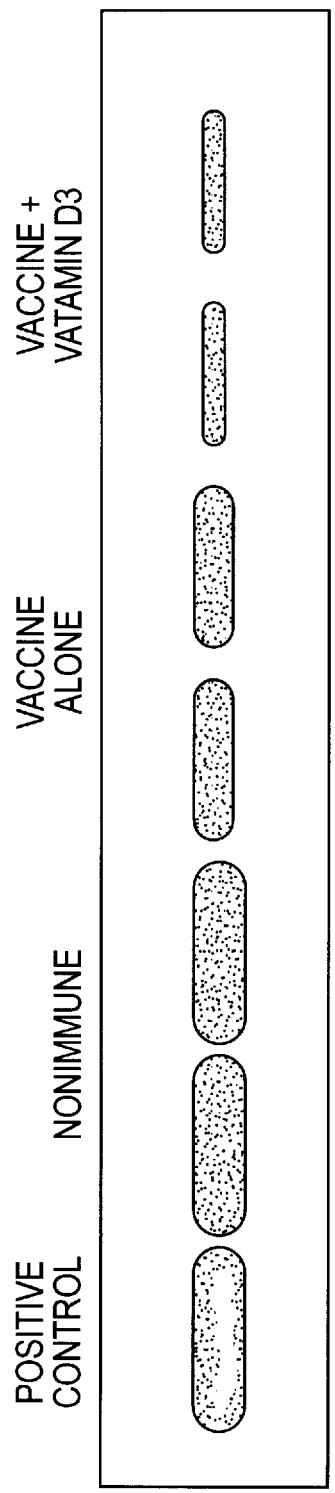
FIG. 16C shows the relative level of infectivity of Influenza type A virus detectable by reverse transcriptase polymerase chain reaction in the tracheae.

Administration of $1,25(OH)_2D_3$ in Vaccine Enhances Neutralizing Activity in Mucosal Secretions Balb/c mice, aged 7 weeks, were immunized by an intramuscular route with 0.1 gm of Influenza Type A antigen with or without 100 ng of 1,25 Vitamin $D_3$ in saline. A third group was injected with saline alone. After 8 weeks, all mice were challenged with 100 infectious virus of the same type and strain as the vaccine by the intranasal route. The experiment was terminated three days after challenge to collect nasal wash and tracheae from individual mice. FIG. 16A illustrates the titre of specific antibody in the nasal wash fluid of each mouse in each of three experimental groups. FIG. 16B illustrates the specific neutralizing activity of nasal wash fluids as measured by hemagglutination inhibition. FIG. 16C illustrates the relative level of infectivity of Influenza type A virus detectable by reverse phase polymerase chain reaction in the tracheae of mice from each group. Specific ELISA titres and specific neutralizing activity of nasal wash fluids were significantly higher among those mice immunized with antigen and 1,25 Vitamin $D_3$. Most convincing was the faster clearance of virus from tracheae in mice vaccinated with Influenza antigen and 1,25 Vitamin $D_3$.

EXAMPLE 20

Figure 17A:
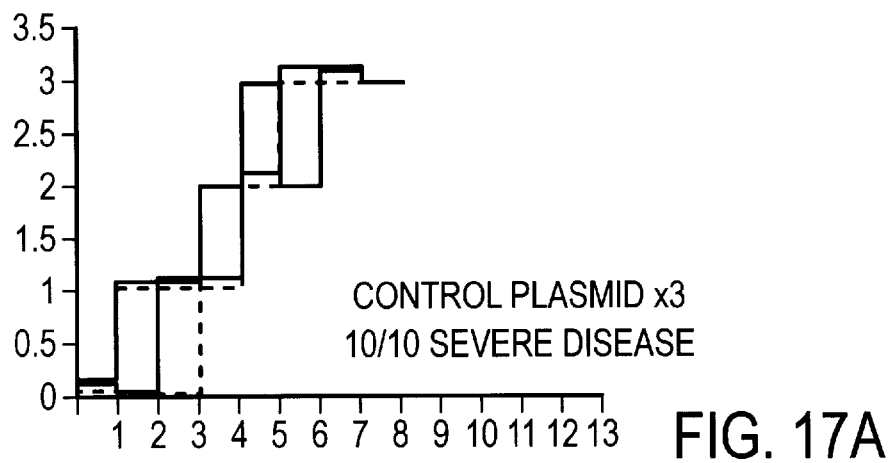
FIGS. 17A–C show the development of clinical disease over time after infection.
Figure 17B:
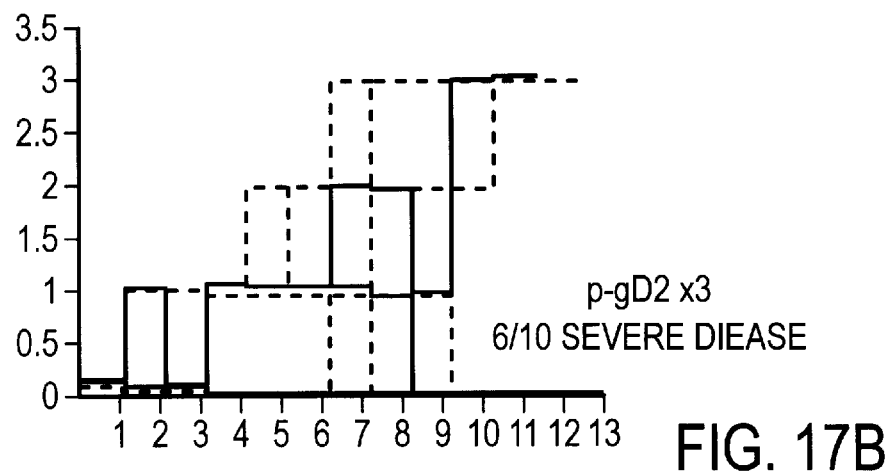
Figure 17C:
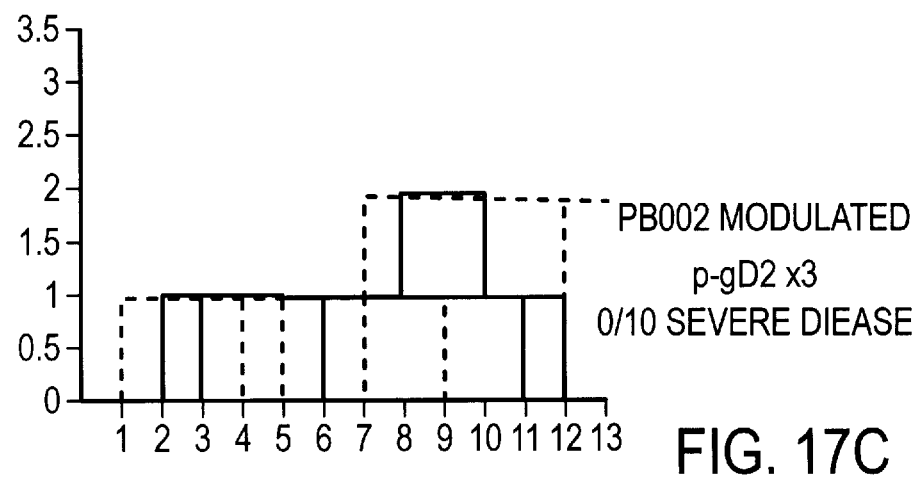
Figure 18:
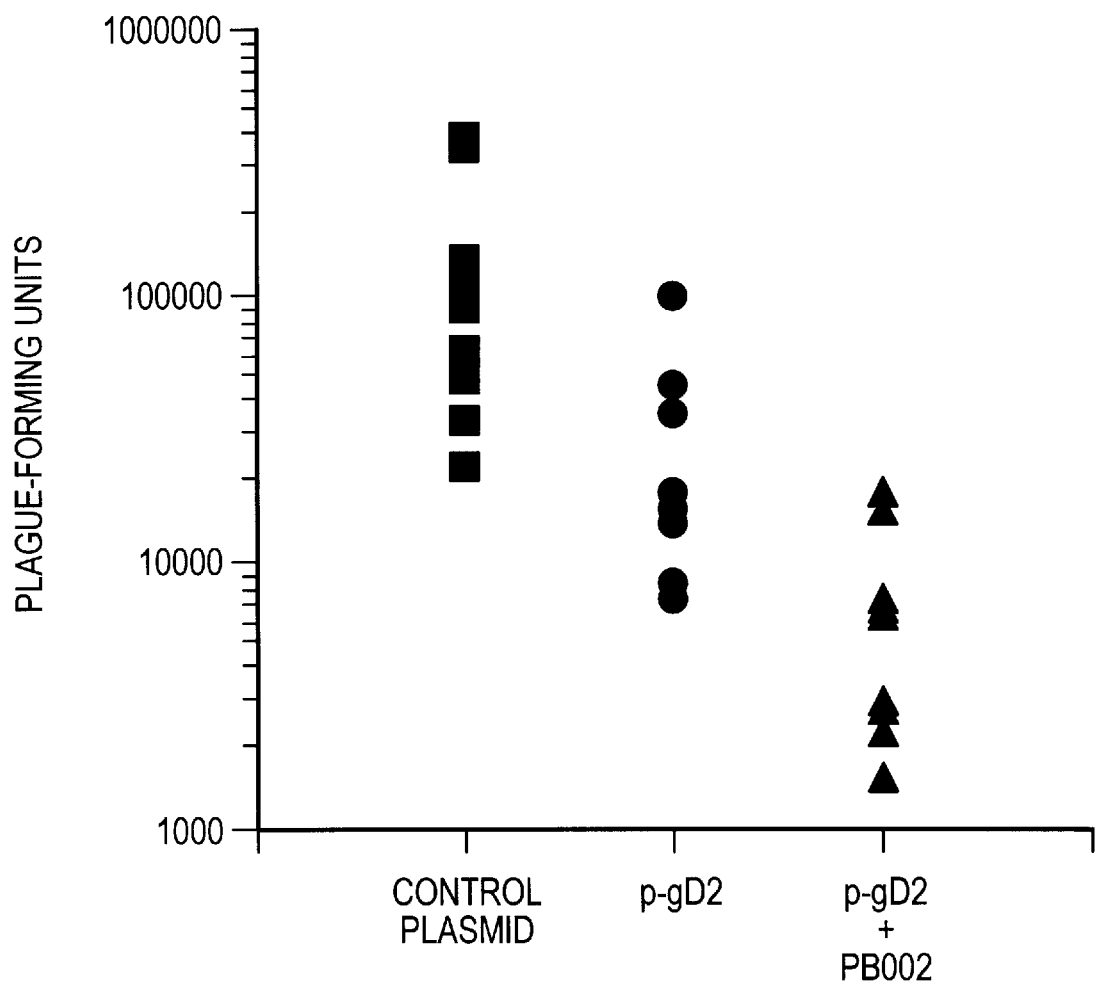
FIG. 18 shows the relative titre of virus detectable in vaginal wash fluids over the first 48 hours following infection.
Figure 19:
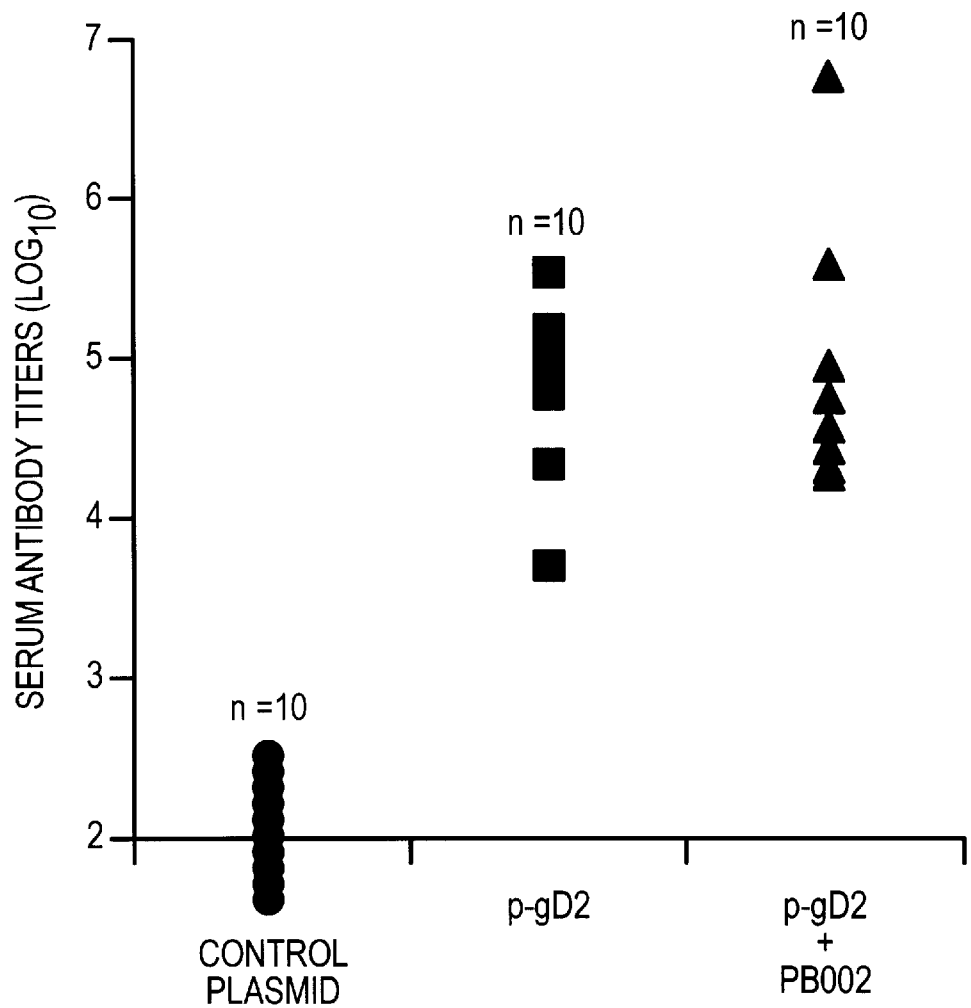
FIG. 19 shows the serum neutralizing activity six days after challenge.

Administration of $1,25(OH)_2D_3$ in DNA Vaccine Enhances Development of Specific Immunity to the Antigen Groups of 10 Balb/c mice were immunized with a DNA vaccine carrying the gene for the gD2 protein of Herpes Simplex Virus type 2. Animals received either a control vaccine which should induce a specific state of immunity or the plasmid containing the gD2 gene with or without 1,25 Vitamin $D_3$ adjuvant. Following three weekly immunizations, mice were challenged intravaginally with infectious Herpes Simplex type 2 virus. FIGS. 17A–C depict the development of clinical disease over time after infection in each mouse. All 10 mice in the control (no specific immunity) developed severe disease quickly. Of the mice that were immunized with the DNA vaccine with the gD2 gene (specific immunity) 60% developed severe disease. Among the group of mice immunized with gD2 DNA vaccine plus 1,25 Vitamin $D_3$, none of the mice developed severe disease. FIG. 8 shows the relative titre of virus detectable in vaginal wash fluids over the first 48 hours following infection. FIG. 19 shows the same neutralizing activity six days after challenge. It was concluded that mice immunized with a vaccine containing 1,25 Vitamin $D_3$ not only developed specific immunity, as dictated by the immunogen, but developed a better quality of immunity that enhanced the rate of clearance of the pathogen and reduced or prevented significant disease.

EXAMPLE 21

Figure 20:
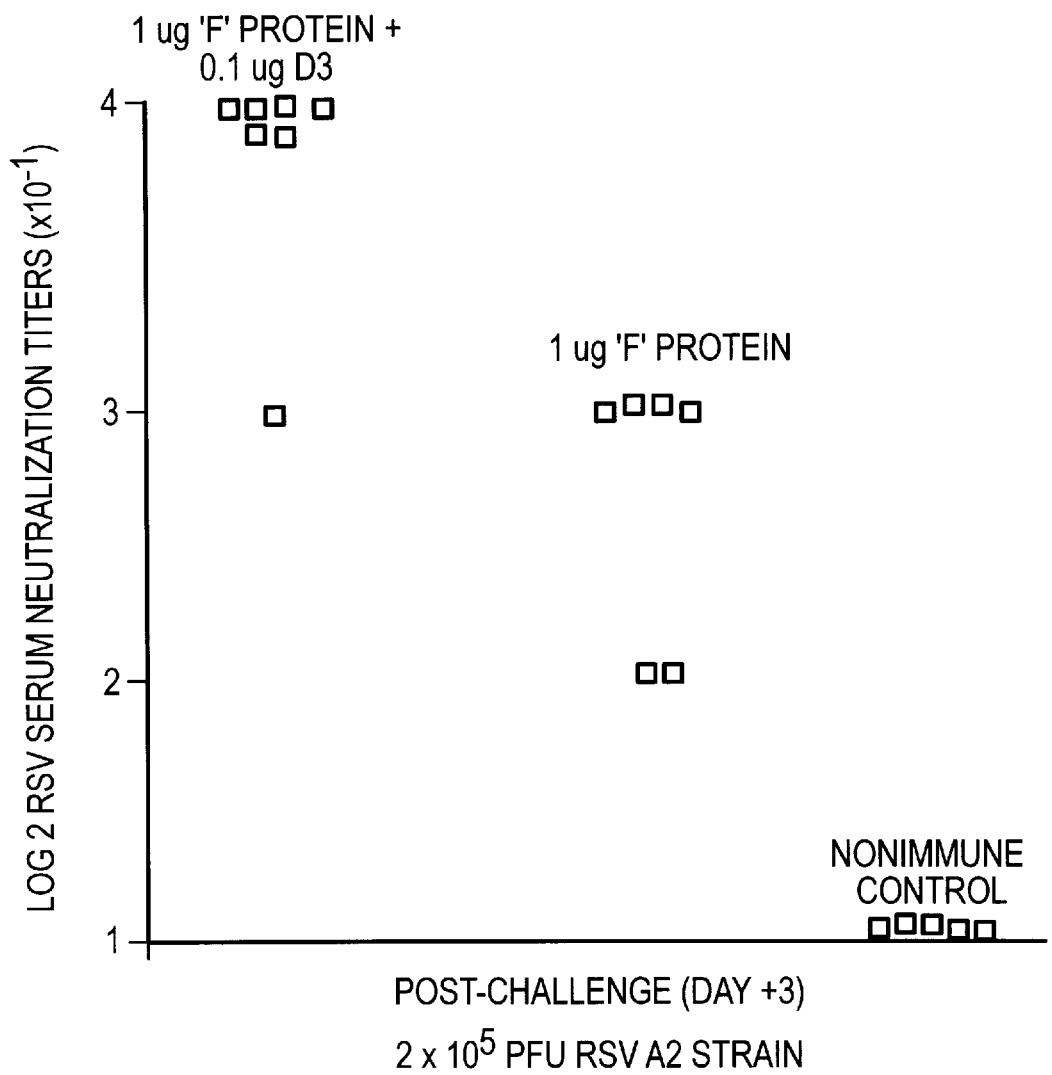
FIG. 20 shows serum neutralizing antibody titres following intranasal challenge with antigen.

Administration of $1,25(OH)_2D_3$ in Vaccine Enhances Neutralizing Activity in Serum and Mucosal Secretions Groups of two-week mice were immunized with 1 μg respiratory syncytial virus (RSV) F protein intramuscularly. One group was immunized with antigen in vehicle and a second group was immunized with the antigen and 0.1 μg 1,25(OH)$_2$D$_3$. Each group was challenged intranasally with RSV F protein. The neutralizing activity of nasal wash fluids and serum was examined three days post-challenge. The results are shown in FIGS. 20 and 21 for serum and nasal washes, respectively. These results demonstrate a significant level of protection in the young mice immunized with the antigen and 1,25(OH)$_2$D$_3$.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

What is claimed is:

1. A method for inducing an antigen-specific mucosal immune response in a vertebrate animal, comprising administering an effective amount of a lymphoid organ modifying agent selected form the group consisting of 1,25-dihydroxy-16-ene Vitamin D$_3$ and calcipotriene to the vertebrate animal at a peripheral, non-mucosal site which drains into a peripheral lymphoid organ or compartment, and administering an effective amount of a specific antigen to the vertebrate animal at a peripheral, non-mucosal site which drains into said peripheral lymphoid organ or compartment.

2. The method of claim 1 wherein said lymphoid organ modifying agent is administered intramuscularly.

3. The method of claim 1 wherein said lymphoid organ modifying agent is administered intradermally.

4. The method of claim 1 wherein said lymphoid organ modifying agent is administered subcutaneously.

5. The method of claim 1 wherein said effective amount of said lymphoid organ modifying agent is 0.01–5.0 μg/kg body weight.

6. The method of claim 1 wherein said effective amount of said lymphoid organ modifying agent is in the range of 0.1–500 μg.

7. The method of claim 1 wherein said lymphoid organ modifying agent administering step commences at a time up to 24 hours earlier than the time said specific antigen administering step commences.

8. The method of claim 1 wherein said lymphoid organ modifying agent administering step commences at about the same time as said specific antigen administering step commences.

9. The method of claim 1 wherein said lymphoid organ modifying agent administering step commences at a time up to 6 days later than the time said specific antigen administering step commences.

10. The method of claim 1 wherein said lymphoid organ modifying agent administering step and said specific antigen administering step are carried out at least partly concurrently.

11. The method of claim 1 wherein said specific antigen and said lymphoid organ modifying agent are combined prior to said administering steps.

12. The method of claim 1 which further comprises administering an effective amount of a dehydroepiandrosterone (DHEA) congener.

13. The method of claim 12 wherein said DHEA congener has the formula

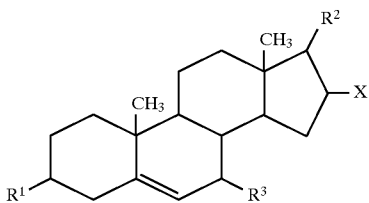

wherein
X is H or halogen;
R$^1$, R$^2$ and R$^3$ are independently =O, —OH, —SH, H, halogen, pharmaceutically acceptable ester, pharmaceutically acceptable thioester, pharmaceutically acceptable ether, pharmaceutically acceptable thioether, pharmaceutically acceptable inorganic esters, pharmaceutically acceptable monosaccharide, disaccharide or oligosaccharide, spirooxirane, spirothirane, —OSO$_2$R$^5$ or —OPOR$^5$R$^6$;
R$^5$ and R$^6$ are independently —OH, pharmaceutically acceptable esters or pharmaceutically acceptable ethers; and
pharmaceutically acceptable salts.

14. The method of claim 12 wherein said effective amount of DHEA congener is 10–1,000 μg when administration is by injection, or 10–100 mg/day when administration is oral.

15. The method of claim 12 wherein said DHEA congener is administered separately from said lymphoid organ modifying agent.

16. The method of claim 15 wherein said DHEA congener is administered up to 14 days prior to said lymphoid organ modifying agent.

17. The method of claim 12 wherein said DHEA congener is administered concurrently with said lymphoid organ modifying agent.

18. The method of claim 12 wherein said DHEA congener is administered separately from said lymphoid organ modifying agent and said antigen.

19. The method of claim 18 wherein said DHEA congener is administered up to 14 days prior to said lymphoid organ modifying agent and said antigen.

20. The method of claim 18 wherein said DHEA congener is administered up to 6 hours after said lymphoid organ modifying agent derivative and said antigen.

21. The method of claim 12 wherein said antigen, lymphoid organ modifying agent and said DHEA congener are combined prior to administration.

22. A method for inducing production of antigen-specific antibodies in the mammary secretions of a female mammal, comprising treating the female mammal according to the method of claim 1.

23. A method for inducing production of antigen-specific antibodies in the mammary secretions of a female mammal, comprising treating the female mammal according to the method of claim 12.

24. A method for conferring a specific passive immunity to a suckling mammal, comprising permitting the suckling mammal to consume mammary secretions from a female mammal treated according to the method of claim 1.

25. A method for conferring a specific passive immunity to a suckling mammal, comprising permitting the suckling mammal to consume mammary secretions from a female mammal treated according to the method of claim 12.

26. A method for inducing an antigen-specific mucosal immune response in a vertebrate animal, which comprises administering an effective amount of at least one lymphoid organ modifying agent selected from the group of 1,25(OH)$_2$D$_3$ or all trans-retinoic acid to the vertebrate animal at a peripheral, non-mucosal site which drains into a peripheral lymphoid organ or compartment, administering an effective amount of a dehydroepiandrosterone (DHEA) congener to the vertebrate animal and administering an effective amount of a specific antigen to the vertebrate animal at a peripheral, non-mucosal site which drains into said peripheral lymphoid organ or compartment.

27. The method of claim 26 wherein said lymphoid organ modifying agent is 1,25(OH)$_2$D$_3$.

28. The method of claim 26 wherein said lymphoid organ modifying agent is all trans-retinoic acid.

29. The method of claim 26 wherein said lymphoid organ modifying agent is administered intramuscularly.

30. The method of claim 26 wherein said lymphoid organ modifying agent is administered intradermally.

31. The method of claim 26 wherein said lymphoid organ modifying agent is administered subcutaneously.

32. The method of claim 26 wherein said effective amount of said lymphoid organ modifying agent is 0.01–5.0 $\mu$g/kg body weight.

33. The method of claim 26 wherein said effective amount of said lymphoid organ modifying agent is in the range of 0.1–500 $\mu$g.

34. The method of claim 26 wherein said lymphoid organ modifying agent administering step, said specific antigen administering step and said DHEA congener administering step are carried out at least partly concurrently.

35. The method of claim 26 wherein said specific antigen, said lymphoid organ modifying agent and said DHEA congener are combined prior to said administering steps.

36. The method of claim 26 wherein said DHEA congener has the formula

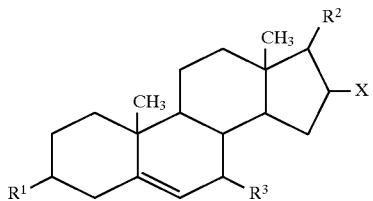

wherein
X is H or halogen;
R$^1$, R$^2$ and R$^3$ are independently =O, —OH, —SH, H, halogen, pharmaceutically acceptable ester, pharmaceutically acceptable thioester, pharmaceutically acceptable ether, pharmaceutically acceptable thioether, pharmaceutically acceptable inorganic esters, pharmaceutically acceptable monosaccharide, disaccharide or oligosaccharide, spirooxirane, spirothirane, —OSO$_2$R$^5$ or —OPOR$^5$R$^6$;
R$^5$ and R$^6$ are independently —OH, pharmaceutically acceptable esters or pharmaceutically acceptable ethers; and
pharmaceutically acceptable salts,
with the proviso that when R$^2$ is =O, R$^3$ is H, and X is H or halogen, then R$^1$ is not —OH, —SH, —OSO$_2$R$^5$ or —OPOR$^5$R$^6$, where R$^5$ and R$^6$ are independently a straight or branched C$_{1-14}$ alkyl.

37. The method of claim 26 wherein said effective amount of DHEA congener is 10–1,000 $\mu$g when administration is by injection, or 10–100 mg/day when administration is oral.

38. The method of claim 36 wherein said lymphoid organ modifying agent is 1,25(OH)$_2$D$_3$.

39. The method of claim 36 wherein said lymphoid organ modifying agent is all trans-retinoic acid.

40. The method of claim 26 wherein said DHEA congener is administered separately from said lymphoid organ modifying agent.

41. The method of claim 40 wherein said DHEA congener is administered up to 14 days prior to said lymphoid organ modifying agent.

42. The method of claim 26 wherein said DHEA congener is administered concurrently with said lymphoid organ modifying agent.

43. The method of claim 26 wherein said DHEA congener is administered separately from said lymphoid organ modifying agent and said antigen.

44. The method of claim 43 wherein said DHEA congener is administered up to 14 days prior to said lymphoid organ modifying agent and said antigen.

45. The method of claim 43 wherein said DHEA congener is administered up to 6 hours days after said lymphoid organ modifying agent and said antigen.

46. The method of claim 26 wherein said antigen, lymphoid organ modifying agent and said DHEA congener are combined prior to administration.

47. A method for inducing production of antigen-specific antibodies in the mammary secretions of a female mammal, comprising treating the female mammal according to the method of claim 26.

48. A method for conferring a specific passive immunity to a suckling mammal, comprising permitting the suckling mammal to consume mammary secretions from a female mammal treated according to the method of claim 26.

49. A vaccine composition comprising an effective amount of a lymphoid organ modifying agent selected form the group consisting of 1,25-dihydroxy-16-ene Vitamin D$_3$ and calcipotriene and an effective amount of a specific antigen in a pharmaceutically acceptable carrier to induce an antigen-specific mucosal immune response.

50. The vaccine composition of claim 49 which further comprises an effective amount of a dehydroepiandrosterone (DHEA) congener to enhance an antigen-specific immune response.

51. The vaccine composition of claim 50 wherein said DHEA congener has the formula

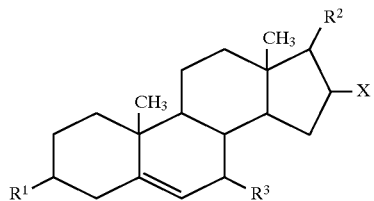

wherein
X is H or halogen;
R$^1$, R$^2$ and R$^3$ are independently =O, —OH, —SH, H, halogen, pharmaceutically acceptable ester, pharmaceutically acceptable thioester, pharmaceutically acceptable ether, pharmaceutically acceptable thioether, pharmaceutically acceptable inorganic esters, pharmaceutically acceptable monosaccharide, disaccharide or oligosaccharide, spirooxirane, spirothirane, —OSO$_2$R$^5$ or —OPOR$^5$R$^6$;
R$^5$ and R$^6$ are independently —OH, pharmaceutically acceptable esters or pharmaceutically acceptable ethers; and
pharmaceutically acceptable salts.

52. The vaccine composition of claim 49 wherein said antigen is capable of eliciting an immune response against viral hepatitis, influenza, diphtheria, tetanus, pertussis, measles, mumps, rubella, polio, pneumococcus, herpes, respiratory syncytial virus, haemophilus influenza type b, varicella-zoster virus or rabies.

53. The vaccine composition of claim 50 wherein said antigen is capable of eliciting an immune response against viral hepatitis, influenza, diphtheria, tetanus, pertussis, measles, mumps, rubella, polio, pneumococcus, herpes, respiratory syncytial virus, haemophilus influenza type b, varicella-zoster virus or rabies.

54. A vaccine composition comprising an effective amount of at least one lymphoid organ modifying agent selected from the group consisting of 1,25-dihydroxy Vitamin $D_3$ (1,25(OH)$_2$D$_3$) and all trans-retinoic acid, an effective amount of a dehydroepiandrosterone (DHEA) congener, and effective amount of a specific antigen in a pharmaceutically acceptable carrier to induce an antigen-specific mucosal immune response.

55. The vaccine composition of claim 54 wherein said lymphoid organ modifying agent is 1,25(OH)$_2$D$_3$.

56. The vaccine composition of claim 54 wherein said lymphoid organ modifying agent is all trans-retinoic acid.

57. The vaccine composition of claim 54 wherein said DHEA congener has the formula

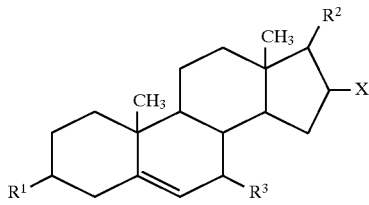

wherein

X is H or halogen;

$R^1$, $R^2$ and $R^3$ are independently =O, —OH, —SH, H, halogen, pharmaceutically acceptable ester, pharmaceutically acceptable thioester, pharmaceutically acceptable ether, pharmaceutically acceptable thioether, pharmaceutically acceptable inorganic esters, pharmaceutically acceptable monosaccharide, disaccharide or oligosaccharide, spirooxirane, spirothirane, —OSO$_2$R$^5$ or —OPOR$^5$R$^6$;

$R^5$ and $R^6$ are independently —OH, pharmaceutically acceptable esters or pharmaceutically acceptable ethers; and pharmaceutically acceptable salts, with the proviso that when $R^2$ is =O, $R^3$ is H, and X is H or halogen, then $R^1$ is not —OH, —SH, —OSO$_2$R$^5$ or —OPOR$^5$R$^6$, where $R^5$ and $R^6$ are independently a straight or branched $C_{1-14}$ alkyl.

58. The vaccine composition of claim 57 wherein said lymphoid organ modifying agent is 1,25(OH)$_2$D$_3$.

59. The vaccine composition of claim 57 wherein said lymphoid organ modifying agent is all trans-retinoic acid.

60. The vaccine composition of claim 54 wherein said antigen is capable of eliciting an immune response against viral hepatitis, influenza, diphtheria, tetanus, pertussis, measles, mumps, rubella, polio, pneumococcus, herpes, respiratory syncytial virus, haemophilus influenza type b, varicella-zoster virus or rabies.

61. The vaccine composition of claim 57 wherein said antigen is capable of eliciting an immune response against viral hepatitis, influenza, diphtheria, tetanus, pertussis, measles, mumps, rubella, polio, pneumococcus, herpes, respiratory syncytial virus, haemophilus influenza type b, varicella-zoster virus or rabies.

* * * * *